United States Patent
Matray et al.

(10) Patent No.: US 11,370,922 B2
(45) Date of Patent: Jun. 28, 2022

(54) ULTRA BRIGHT POLYMERIC DYES WITH PEPTIDE BACKBONES

(71) Applicant: SONY CORPORATION, Tokyo (JP)

(72) Inventors: Tracy Matray, Snohomish, WA (US); Sharat Singh, Rancho Santa Fe, CA (US); Michael VanBrunt, Covington, WA (US)

(73) Assignee: Sony Corporation, Tokyo (JP)

( * ) Notice: Subject to any disclaimer, the term of this patent is extended or adjusted under 35 U.S.C. 154(b) by 712 days.

(21) Appl. No.: 16/099,643

(22) PCT Filed: May 10, 2017

(86) PCT No.: PCT/US2017/031919
§ 371 (c)(1),
(2) Date: Nov. 7, 2018

(87) PCT Pub. No.: WO2017/196954
PCT Pub. Date: Nov. 16, 2017

(65) Prior Publication Data
US 2019/0153232 A1  May 23, 2019

Related U.S. Application Data

(60) Provisional application No. 62/334,243, filed on May 10, 2016.

(51) Int. Cl.
| | | |
|---|---|---|
| C09B 69/00 | (2006.01) | |
| C09B 69/10 | (2006.01) | |
| G01N 33/50 | (2006.01) | |
| C07K 7/06 | (2006.01) | |
| C07K 7/08 | (2006.01) | |
| C07K 17/00 | (2006.01) | |
| C07F 9/09 | (2006.01) | |
| C07F 9/24 | (2006.01) | |
| G01N 33/533 | (2006.01) | |
| G01N 33/58 | (2006.01) | |

(52) U.S. Cl.
CPC ............ *C09B 69/102* (2013.01); *C07F 9/091* (2013.01); *C07F 9/2408* (2013.01); *C07K 7/06* (2013.01); *C07K 7/08* (2013.01); *C07K 17/00* (2013.01); *C09B 69/103* (2013.01); *C09B 69/105* (2013.01); *C09B 69/109* (2013.01); *G01N 33/5005* (2013.01); *G01N 33/533* (2013.01); *G01N 33/582* (2013.01)

(58) Field of Classification Search
CPC .................................................. C09B 69/102
USPC ....................................................... 436/172
See application file for complete search history.

(56) References Cited

U.S. PATENT DOCUMENTS

| | | | |
|---|---|---|---|
| 4,450,305 | A | 5/1984 | Kamhi |
| 4,476,229 | A | 10/1984 | Fino et al. |
| 4,778,753 | A | 10/1988 | Yamanishi et al. |
| 5,053,054 | A | 10/1991 | Kirchanski et al. |
| 5,268,486 | A | 12/1993 | Waggoner et al. |
| 5,318,894 | A | 6/1994 | Pugia |
| 5,994,143 | A | 11/1999 | Bieniarz et al. |
| 6,140,480 | A | 10/2000 | Kool |
| 6,171,859 | B1 | 1/2001 | Herrnstadt et al. |
| 6,218,108 | B1 | 4/2001 | Kool |
| 6,380,431 | B1 | 4/2002 | Whipple et al. |
| 6,479,650 | B1 | 11/2002 | Kool |
| 6,534,041 | B1 | 3/2003 | Licha et al. |
| 6,627,400 | B1 | 9/2003 | Singh et al. |
| 6,670,193 | B2 | 12/2003 | Kool |
| 6,716,452 | B1 | 4/2004 | Piccariello et al. |
| 6,852,709 | B2 | 2/2005 | Leong et al. |
| 7,060,708 | B2 | 6/2006 | Piccariello et al. |
| 7,172,907 | B2 | 2/2007 | Chen et al. |
| 7,423,133 | B2 | 9/2008 | Kool et al. |
| 7,667,024 | B2 | 2/2010 | Mao et al. |
| 7,897,684 | B2 | 3/2011 | Bazan et al. |

(Continued)

FOREIGN PATENT DOCUMENTS

| | | |
|---|---|---|
| CN | 101137735 A | 3/2008 |
| CN | 102174078 A | 9/2011 |

(Continued)

OTHER PUBLICATIONS

Divittorio et al., "Synthetic Peptides with Selective Affinity for Apoptotic Cells," *Organic & Biomolecular Chemistry* 4(10):1966-1976, 2006.

(Continued)

*Primary Examiner* — Christine T Mui
*Assistant Examiner* — Emily R. Berkeley
(74) *Attorney, Agent, or Firm* — Seed IP Law Group LLP

(57) ABSTRACT

Compounds useful as fluorescent or colored dyes are disclosed. The compounds have the following structure (I), including stereoisomers, salts and tautomers thereof, wherein $R^1$, $R^2$, $R^3$, $L^1$, $L^2$, $L^3$, $L^4$, $L^5$, M, m and n are as defined herein. Methods associated with preparation and use of such compounds are also provided.

(I)

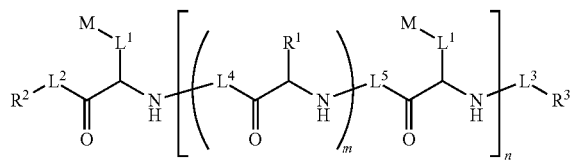

20 Claims, No Drawings

(56) References Cited

U.S. PATENT DOCUMENTS

| | | |
|---|---|---|
| 8,008,522 B2 | 8/2011 | Lukhtanov et al. |
| 8,217,389 B2 | 7/2012 | Nakano et al. |
| 8,293,700 B2 | 10/2012 | Arranz |
| 8,349,308 B2 | 1/2013 | Yurkovetskiy et al. |
| 8,431,545 B2 | 4/2013 | Kataoka et al. |
| 8,802,738 B2 | 8/2014 | Emrick |
| 8,895,023 B2 | 11/2014 | Rademacher et al. |
| 8,906,603 B2 | 12/2014 | Castro et al. |
| 9,085,799 B2 | 7/2015 | Bazan et al. |
| 9,150,782 B2 | 10/2015 | Lee et al. |
| 9,400,273 B1 | 7/2016 | Liu et al. |
| 9,545,447 B2 | 1/2017 | Wooley et al. |
| 9,649,389 B2 | 5/2017 | Groves et al. |
| 9,687,291 B2 | 6/2017 | Shimizu et al. |
| 9,689,877 B2 | 6/2017 | Matray et al. |
| 9,765,220 B2 | 9/2017 | Matray et al. |
| 9,822,134 B2 | 11/2017 | Segev |
| 9,851,359 B2 | 12/2017 | Matray et al. |
| 9,884,070 B2 | 2/2018 | Denardo et al. |
| 9,913,992 B2 | 3/2018 | Demarest et al. |
| 10,036,754 B2 | 7/2018 | Matray et al. |
| 10,191,060 B2 | 1/2019 | Chiu et al. |
| 10,435,563 B2 | 10/2019 | Matray et al. |
| 10,709,791 B2 | 7/2020 | Stayton et al. |
| 10,865,310 B2 | 12/2020 | Matray et al. |
| 10,866,244 B2 | 12/2020 | Matray et al. |
| 10,954,391 B2 | 3/2021 | Matray et al. |
| 10,989,715 B2 | 4/2021 | Matray et al. |
| 11,084,932 B2 | 8/2021 | Battrell et al. |
| 11,142,647 B2 | 10/2021 | Matray et al. |
| 2001/0018503 A1 | 8/2001 | Whipple et al. |
| 2002/0099013 A1 | 7/2002 | Piccariello et al. |
| 2003/0054361 A1 | 3/2003 | Heller |
| 2003/0207208 A1 | 11/2003 | Uenishi |
| 2003/0207264 A1 | 11/2003 | Packard et al. |
| 2004/0014981 A1 | 1/2004 | Lugade et al. |
| 2004/0138467 A1 | 7/2004 | French et al. |
| 2004/0186278 A1 | 9/2004 | Chen et al. |
| 2004/0224372 A1 | 11/2004 | Li et al. |
| 2004/0241768 A1 | 12/2004 | Whitten et al. |
| 2005/0054024 A1 | 3/2005 | Lawrence |
| 2005/0123935 A1 | 6/2005 | Haugland et al. |
| 2006/0008822 A1 | 1/2006 | Manoharan et al. |
| 2006/0035302 A1 | 2/2006 | Lee |
| 2006/0063186 A1 | 3/2006 | Benson et al. |
| 2007/0042398 A1 | 2/2007 | Peng et al. |
| 2007/0077549 A1 | 4/2007 | Buller et al. |
| 2007/0148094 A1 | 6/2007 | Uzgiris et al. |
| 2007/0269902 A1 | 11/2007 | Beechem et al. |
| 2008/0227939 A1 | 9/2008 | Mizoshita et al. |
| 2009/0253792 A1 | 10/2009 | Mickle et al. |
| 2009/0299070 A1 | 12/2009 | Berens et al. |
| 2010/0039684 A1 | 2/2010 | Kolb et al. |
| 2010/0092386 A1 | 4/2010 | Segev |
| 2010/0129800 A1 | 5/2010 | Aymami Bofarull et al. |
| 2010/0192312 A1 | 8/2010 | Cremer et al. |
| 2011/0224516 A1 | 9/2011 | Romey et al. |
| 2012/0021454 A1 | 1/2012 | Bikker et al. |
| 2012/0116079 A1 | 5/2012 | Lukhtanov et al. |
| 2012/0126175 A1 | 5/2012 | Ueno et al. |
| 2013/0059343 A1 | 3/2013 | Cheung |
| 2013/0102021 A1 | 4/2013 | Beacham et al. |
| 2013/0119363 A1 | 5/2013 | Sasaki et al. |
| 2013/0137755 A1 | 5/2013 | Segev |
| 2013/0202536 A1 | 8/2013 | Mustaev et al. |
| 2013/0244891 A1 | 9/2013 | Waggoner et al. |
| 2015/0110715 A1 | 4/2015 | Eder et al. |
| 2015/0159198 A1 | 6/2015 | McGall et al. |
| 2015/0232615 A1 | 8/2015 | Kwiatkowski |
| 2015/0258217 A1 | 9/2015 | Caravan et al. |
| 2016/0039850 A1 | 2/2016 | Segev |
| 2016/0176903 A1 | 6/2016 | Segev |
| 2016/0264737 A1 | 9/2016 | Bartholomew et al. |
| 2016/0327859 A1 | 11/2016 | Idei et al. |
| 2016/0347907 A1 | 12/2016 | Dose |
| 2017/0286113 A1 | 10/2017 | Shanbhogue et al. |
| 2017/0326233 A1 | 11/2017 | Demeule et al. |
| 2018/0065998 A1 | 3/2018 | Battrell et al. |
| 2018/0079909 A1 | 3/2018 | Matray et al. |
| 2018/0163052 A1 | 6/2018 | Matray et al. |
| 2018/0164322 A1 | 6/2018 | Matray et al. |
| 2018/0237641 A1 | 8/2018 | Matray et al. |
| 2019/0016898 A1 | 1/2019 | Matray et al. |
| 2019/0136065 A1 | 5/2019 | Singh et al. |
| 2019/0144678 A1 | 5/2019 | Matray et al. |
| 2019/0177549 A1 | 6/2019 | Matray et al. |
| 2019/0300716 A1 | 10/2019 | Matray et al. |
| 2020/0109287 A1 | 4/2020 | Matray et al. |
| 2020/0222554 A1 | 7/2020 | Matray et al. |
| 2020/0284798 A1 | 9/2020 | Matray et al. |
| 2020/0353089 A1 | 11/2020 | Matray |
| 2020/0353094 A1 | 11/2020 | Matray |
| 2020/0360526 A1 | 11/2020 | Matray |
| 2020/0392345 A1 | 12/2020 | Matray et al. |
| 2021/0032277 A1 | 2/2021 | Matray et al. |
| 2021/0032474 A1 | 2/2021 | Matray et al. |
| 2021/0095130 A1 | 4/2021 | Matray et al. |
| 2021/0096135 A1 | 4/2021 | Matray et al. |
| 2021/0109104 A1 | 4/2021 | Jackson et al. |
| 2021/0128591 A1 | 5/2021 | Matray |
| 2021/0128739 A1 | 5/2021 | Matray |
| 2021/0253864 A1 | 8/2021 | Matray et al. |
| 2021/0261782 A1 | 8/2021 | Matray et al. |
| 2021/0285953 A1 | 9/2021 | Matray et al. |
| 2021/0340380 A1 | 11/2021 | Matray et al. |
| 2021/0395530 A1 | 12/2021 | Matray et al. |

FOREIGN PATENT DOCUMENTS

| | | |
|---|---|---|
| CN | 102971283 A1 | 3/2013 |
| CN | 103319378 A | 9/2013 |
| CN | 104072727 A | 10/2014 |
| CN | 106589005 A | 4/2017 |
| EP | 0 708 837 A1 | 5/1996 |
| EP | 1 650 269 A2 | 4/2006 |
| EP | 1 655 317 A1 | 5/2006 |
| EP | 2 366 785 A1 | 9/2011 |
| GB | 2 372 256 A | 8/2002 |
| GB | 2 456 298 A | 7/2009 |
| GB | 2 554 666 A | 4/2018 |
| JP | S61-207395 A | 9/1986 |
| JP | 4-282391 A | 10/1992 |
| JP | 2000-17183 A | 1/2000 |
| JP | 2008-510041 A | 4/2008 |
| JP | 2008-535945 A | 9/2008 |
| JP | 2009-519595 A | 5/2009 |
| JP | 2010-508295 A | 3/2010 |
| KR | 10-1041446 B1 | 6/2011 |
| KR | 10-2015-0007795 A | 1/2015 |
| SU | 1121931 A | 4/1988 |
| WO | 93/06482 A1 | 4/1993 |
| WO | 94/13688 A1 | 6/1994 |
| WO | 95/02700 A1 | 1/1995 |
| WO | 01/69254 A2 | 9/2001 |
| WO | 01/73123 A2 | 10/2001 |
| WO | 01/83502 A1 | 11/2001 |
| WO | 02/22883 A1 | 3/2002 |
| WO | 02/36832 A2 | 5/2002 |
| WO | 2006/020947 A2 | 2/2006 |
| WO | 2006/099050 A2 | 9/2006 |
| WO | 2009/015467 A1 | 2/2009 |
| WO | 2010/026957 A1 | 3/2010 |
| WO | 2013/012687 A2 | 1/2013 |
| WO | 2014/043289 A2 | 3/2014 |
| WO | 2014/102803 A1 | 7/2014 |
| WO | 2014/144793 A1 | 9/2014 |
| WO | 2014/147642 A1 | 9/2014 |
| WO | 2014/159392 A1 | 10/2014 |
| WO | 2015/027176 A1 | 2/2015 |
| WO | 2015/109136 A2 | 7/2015 |
| WO | 2016/138461 A1 | 9/2016 |
| WO | 2016/183185 A1 | 11/2016 |
| WO | 2017/173348 A1 | 10/2017 |
| WO | 2017/177065 A2 | 10/2017 |

(56) References Cited

FOREIGN PATENT DOCUMENTS

| | | |
|---|---|---|
| WO | 2018/060722 A1 | 4/2018 |
| WO | 2019/071208 A1 | 4/2019 |
| WO | 2021/062176 A2 | 4/2021 |
| WO | 2021/067483 A1 | 4/2021 |

OTHER PUBLICATIONS

Beaucage et al., "The Functionalization of Oligonucleotides via Phosphoramidite Derivatives," *Tetrahedron* 49(10):1925-1963, 1993.
Chattopadhyay et al., "Brilliant Violet Fluorophores: A New Class of Ultrabright Fluorescent Compounds for Immunofluorescence Experiments," *Cytometry Part A* 81A:456-466, 2012.
Cuppoletti et al., "Oligomeric fluorescent labels for DNA," *Bioconjug. Chem.* 16(3):528-534, 2005.
Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.
Dubrovsky, "Semiconductor nanoparticles as reporters in multiplexed immunoassay and cell analysis," *International Journal of Nanoscience* 8(1 & 2):163-167, 2009.
Jain et al. "Current ADC Linker Chemistry," *Pharm. Res.* 32:3526-3540, 2015.
Kozma et al., "Fluorescent Ligands for Adenosine Receptors," *Bioorganic & Medicinal Chemistry Letters* 23: 26-36, 2013.
Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.
Li et al., "Polymeric Drugs: Advances in the development of pharmacologically active polymers," *Journal of Controlled Release* 219:360-382, 2015.
Luo et al., "Sensitive and rapid quantification of C-reactive protein using quantum dot-labeled microplate immunoassay," *Journal of Translational Medicine* 10(24):1-9, 2012.
Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.
Paris et al., "Probing DNA sequences in solution with a monomer-excimer fluorescence color change," *Nucleic Acids Research* 26(16):3789-3793, 1998.
Petreus et al., "Polyester imides containing main-chain phosphorus," *Revue Roumaine de Chimie* 34(8):971-978, 1994 (with English Abstract).
Ren et al., "An Antisense Oligodeoxynucleotide-Doxorubicin Conjugate: Preparation and Its Reversal Multidrug Resistance of Human Carcinoma Cell Line In Vitro," *Nucleosides, Nucleotides & Nucleic Acids* 23(10):1595-1607, 2004.
RN 230952-79-1, Registry Database Compound, 1999.
Singh et al., "Multiplexed measurement of membrane protein populations," *Caplus* 2003:769075, 2003. (2 pages).
Stuart et al., "Site-Specific DNA-Doxorubicin Conjugates Display Enhanced Cytotoxicity to Breast Cancer Cells," *Bioconjugate Chemistry* 25:406-413, 2014.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Tram et al., "Oligonucleotide Labeling Using BODIPY Phosphoramidite," *Nucleosides, Nucleotides & Nucleic Acids* 30(1):1-11, 2011.
Avirah et al., "Infrared Absorbing Croconaine Dyes: Synthesis and Metal Ion Binding Properties," *J. Org. Chem.* 73(1):274-279, 2008.
Li et al., "Responsive nanogel-based dual fluorescent sensors for temperature and $Hg^{2+}$ ions with enhanced detection sensitivity," *J. Mater. Chem.* 20:10716-10723, 2010.
Stewart et al., "The Fluorescence of a Chelating Two-Photon-Absorbing Dye is Enhanced with the Addition of Transition Metal Ions but Quenched in the Presence of Acid," *Proc. of SPIE* 9939(993904):1-10, 2016.
Zhang et al., "FRET Imaging of Enzyme-Responsive HPMA Copolymer Conjugate," *Macromolecular Bioscience* 17(1600215):1-8, 2017.
Doi et al., "Hetero-Selective DNA-Like Duplex Stabilized by Donor-Acceptor Interactions," *Chem. Eur. J.* 21:15974-15980, 2015.
Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.
Johansson, "Choosing Reporter-Quencher Pairs for Efficient Quenching Through Formation of Intramolecular Dimers," *Methods in Molecular Biology* 335:17-29, 2006.
Masuko et al., "Fluorescence resonance energy transfer from pyrene to perylene labels for nucleic acid hybridization assays under homogenous solution conditions," *Nucleic Acids Research* 28(8):e34, 2000 (8 pages).
Saito et al., "Dual-labeled oligonucleotide probe for sensing adenosine via FRET: A novel alternative to SNPs genotyping," *Chem. Commun.*:2133-2135, 2007.
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, 2002.
Vinogradov et al., "Total synthesis and biochemical characterization of mirror image barnase," *Chem Sci.* 6: 2997-3002, 2015.
"What is an Analyte?," Google Search, dated Mar. 22, 2018, retrieved from https://www.google.com/search?q-what+is+an+analyte&rlz=1C1GCEB_enUS775US775&oq=what+is+an+analyte&aqs=chrome..69i57j0I5.32321jOj7&s . . . 2 pages.
Arian et al., "1,9-Dialkoxyanthracene as a 1O2-Sensitive Linker," *J. Am. Chem. Soc.* 133:3972-3980, 2011.
Babitskaya et al., "Bromoacyl Analogues of Phosphatidylcholine with Intramolecular Fluorescence Quenching and Their Use as Substrates for Continuous Monitoring of Phospholipase A2 Activity," *Applied Biochemistry and Microbiology* 40(4):351-356, 2004.
Becker et al., "New Thermotropic Dyes on Amino-Subsituted Perylendicarboximides," *Chem. Eur. J.* 6(21):3984-3990, 2000.
Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016. (8 pages).
Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015, 1 page.
Bergstrom et al., "Potent Promise," *Innovations in Pharmaceutical Technology* 49:16-20, 2014.
Bergstrom et al., "XMT-1522 induces tumor regressions in pre-clinical models representing HER2-positive and HER2 low-expressing breast cancer," Mersana Therapeutics, Abstract P4-14-28, 2015, 1 page.
Braeckmans et al., "Three-dimensional fluorescence recovery after photobleaching with the confocal scanning laser microscope," *Biophysical Journal* 85:2240-2252, 2003.
Braga et al., "Intracellular macromolecular mobility measured by fluorescence recovery after photobleaching with confocal laser scanning microscopes," *Molecular Biology of the Cell* 15:4749-4760, 2004.
Brinkley, "A brief survey of methods for preparing protein conjugates with dyes, haptens and crosslinking reagents," *Bioconjugate Chem* 3:2-13, 1992.
CAPLUS Accession No. 1975: 171341, Holy, "Nucleic acid components and their analogs. CLXXII. Aliphatic analogs of nucleosides, nucleotides, and oligonucleotides," Collection of Czechoslovak Chemical Communications 40(1):187-214, 1975. (1 page).

(56) References Cited

OTHER PUBLICATIONS

Chong et al., "Oxygen Quenching of Pyrene-Lipid Fluorescence in Phosphatidylcholine Vesicles—A Probe for Membrane Organization," *Biophys. J.* 47:613-621, 1985.

Dai et al., "DNA-polyfluorophore excimers as sensitive reporters for esterases and lipases," *Chemical Communications* 46(8):1221, 2010. (9 pages).

Gao et al., "Libraries of Composite Polyfluors Built from Fluorescent Deoxyribosides," *Jorunal of the American Chemical Society* 124(39):11590-11591, 2002.

Gao et al., "Modified DNA Analogues That Sense Light Exposure with Color Change," *Journal of the American Chemical Society* 126(40):12748-12749, 2004.

Gordon et al., "Analysis of simulated and experimental fluorescence recovery after photobleaching. Data for two diffusing components," *Biophysical Journal* 68:766-778, 1995.

Hanhela et al., "Synthesis and evaluation of fluorescent materials for colour control of peroxyoxalate chemiluminescence. II. Violet and blue emitters," *Australian Journal of Chemistry* 34(8):1701-1717, 1981.

Haraguchi, "Live Cell Imaging: Approaches for Studying Protein Dynamics in Living Cells," *Cell Structure and Function* 27:333-334, 2002.

Koo et al., "Fluorescent DNA chemosensors: identification of bacterial species by their volatile metabolites," *Chemical Communications* 47(41):11435, 2011.

Lee et al., "Monitoring the Hydrophobic Interactions of Internally Pyrene-Labeled Poly(ethylene oxides)s in Water by Fluorescence Spectroscopy," *Macromolecules* 31:9193-9200, 1998.

Liu et al., "Detection of prostate-specific membrane antigen on HUVECs in response to breast tumor-conditioned medium," *International Journal of Oncology* 38:1349-1355, 2011.

Liu et al., "DNA-Based Micelles: Synthesis, Micellar Properties and Size-Dependent Cell Permeability," *Chem. Eur. J.* 16:3791-3797, 2010. (14 Pages).

Mersana Therapeutics, URL=http://www.mersana.com, download date Jan. 3, 2019, 9 pages.

Molotkovsky et al., "Perylenoyl- and Anthrylvinyl-Labeled Lipids as Membrane Probes," *Biochimica et Biophysica Acta* 778:281-288, 1984.

Nussbaumer et al., "Amplification of Chirality by Supramolecular Polymerization of Pyrene Oligomers," *Angewandte Chemie International Edition* 50(24):5490-5494, 2011.

Pownall et al., "Kinetics of Spontaneous and Plasma-Stimulated Sphingomyelin Transfer," *Biochimica et Biophysica Acta* 712:169-176, 1982.

PubChem, "US20100012929A1-20100121-C00010_4," SID No. 140452858, retrieved Mar. 29, 2016 from URL https://pubchem.ncbi.nlm.nih.gov/substance/140452858, 6 pages.

Wang et al., "Cruciforms: Assembling Single Crystal Micro- and Nanostructures from One to Three Dimensions and Their Applications in Organic Field-Effect Transistors," *Chem. Mater.* 21:2840-2845, 2009.

Wang et al., "DNA Polyfluorophores for Real-Time Multicolor Tracking of Dynamic Biological Systems," *Angewandte Chemie Biological Systems* 51(29):7176-7180, 2012.

Wilson et al., "Efficient Quenching of Oligomeric Fluorophores on a DNA Backbone," *Journal of the American Chemical Society* 129(50):15426-15427, 2007.

Wilson et al., "Oligodeoxyfluorosides: Strong Sequence of Dependence of Fluorescence Emission," *Tetrahedron* 63(17):3427-3433, 2007. (18 Pages).

Yurkovetskiy et al., "Advantages of Polyacetal Polymer-based Antibody Drug Conjugates: Application to Low Expression Targets," Mersana Therapeutics, technical paper #2645, 2014, 1 page.

Aviñó et al., "Solid-phase synthesis of oligomers carrying several chromophore units linked by phosphodiester backbones," *Bioorganic & Medicinal Chemistry Letters* 18:2306-2310, 2008.

Boldyrev et al., "Synthesis and Characteristics of New Fluorescent Probes Based on Cardiolipin," *Russian Journal of Bioorganic Chemistry* 35(2):219-224, 2009.

Buckhout-White et al., "Assembling programmable FRET-based photonic networks using designer DNA scaffolds," *Nature Communications* 5:5615, Dec. 11, 2014. (16 pages).

CAS Registry No. 862288-26-4, American Chemical Society, 2021, 1 page.

De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245-2265, 1994.

Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.

Kashida et al., "A Cationic Dye Triplet as a Unique "Glue" That Can Connect Fully Matched Termini of DNA Duplexes," *Chem. Eur. J.* 17:2614-2622, 2011.

Lewis et al., "Orientation Control of Fluorescence Resonance Energy Transfer Using DNA as a Helical Scaffold," *J. Am. Chem. Soc.* 127:10002-10003, 2005.

Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.

Vybornyi et al., "Formation of Two-Dimensional Supramolecular Polymers by Amphiphilic Pyrene Oligomers," *Angew. Chem. Int. Ed.* 52:114488-11493, 2013.

Wang et al., "Fluorescence-Based Evaluation of the Partitioning of Lipids and Lipidated Peptides into Liquid-Ordered Lipid Microdomains: A Model for Molecular Partitioning into Lipid Rafts," *Biophysical Journal* 79:919-933, Aug. 2000.

Winiger et al., "Long-Distance Electronic Energy Transfer in Light-Harvesting Supramolecular Polymers," *Angew. Chem. Int. Ed.* 53:13609-13613, 2014.

Damian et al., "Synthesis and DNA Interaction of Platinum Complex/Peptide Chimera as Potential Drug Candidates," *Eur. J. Org Chem.* 6161-6170, 2010.

Drescher et al., "General Synthesis and Aggregation Behaviour of New Single-Chain Bolaphospholipids: Variations in Chain and Headgroup Structures," *Chemistry—A European Journal* 14(22):6796-6804, 2008.

Rochat et al., "Water-Soluble Cationic Conjugated Polymers: Response to Electron-Rich Bioanalytes," *J. Am. Chem. Soc.* 135:17703-17706, 2013.

Sun et al., "Dual-Color Fluorescence Imaging of Magnetic Nanoparticles in Live Cancer Cells Using Conjugated Polymer Probes," *Scientific Reports* 6:22368, 2016. (12 pages).

Sun et al., "High yield production of high molecular weight poly-(ethylene glycol)/ α-cyclodextrin polyrotaxanes by aqueous one-pot approach," *Polymer* 53:2884-2889, 2012.

Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).

Teyssot et al., "Aromatic Nitrogen Donors for Efficient Copper(1)-NHC CuAAC under Reductant-Free Conditions," *Eur. J. Org. Chem.* 3507-3515, 2010.

Zhao et al., "Mussel-Inspired One-Pot Synthesis of a Fluorescent and Water-Soluble Polydopamine-Polyethyleneimine Copolymer," *Macromol. Rapid Commun.* 36:909-915, 2015.

U.S. Appl. No. 17/690,862, filed Mar. 9, 2022.

ULTRA BRIGHT POLYMERIC DYES WITH PEPTIDE BACKBONES

BACKGROUND

Field

Embodiments of the present invention are generally directed to dimeric and polymeric fluorescent or colored dyes, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes ("brighter") are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the dimeric and polymeric dyes did not achieve the desired increase in brightness.

There is thus a need in the art for water soluble dyes having an increased molar brightness. Ideally, such dyes and biomarkers should be intensely colored or fluorescent and should be available in a variety of colors and fluorescent wavelengths. The present invention fulfills this need and provides further related advantages.

BRIEF SUMMARY

In brief, the present invention is generally directed to compounds useful as water soluble, fluorescent or colored dyes and probes that enable visual detection of analyte molecules, such as biomolecules, as well as reagents for their preparation. Methods for visually detecting an analyte molecule using the dyes are also described.

Embodiments of the presently disclosed dyes include two or more fluorescent and/or colored moieties covalently linked by an amino acid or peptide linker. In contrast to previous reports of dimeric and/or polymeric dyes, the present dyes are significantly brighter than the corresponding monomeric dye compound. While, not wishing to be bound by theory, it is believed that the linker moiety provides sufficient spatial separation between the fluorescent and/or colored moieties such that intramolecular fluorescence quenching is reduced and/or eliminated.

In addition, certain embodiments of the presently disclosed dyes can be synthesized using automated methods, which build polymers in a step-wise manner and incorporate specific sequences of amino acids or monomers. Such a synthesis is also compatible with a variety of amino acids and other monomers. It should be appreciated that specific amino acid sequences allow certain embodiments to be tailored to include desired tertiary structures. Certain embodiments may be synthesized in a manner that allows chromophores to be easily incorporated and/or allows post polymerization modification.

The water soluble, fluorescent or colored dyes of the invention are intensely colored and/or fluorescent and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained.

In one embodiment, compounds having the following structure (I) are provided:

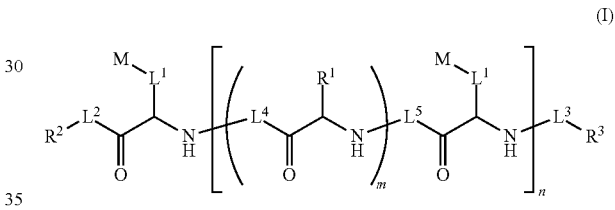

(I)

or a stereoisomer, tautomer or salt thereof, wherein $R^1$, $R^2$, $R^3$, $L^1$, $L^2$, $L^3$, $L^4$, $L^5$, M, m and n are as defined herein.

In another embodiment, a method for staining a sample is provided, the method comprises adding to said sample a representative compound as described herein in an amount sufficient to produce an optical response when said sample is illuminated at an appropriate wavelength.

In still other embodiments, the present disclosure provides a method for visually detecting an analyte molecule, comprising:

(a) providing a representative compound described herein; and (b) detecting the compound by its visible properties.

Other disclosed methods include a method for visually detecting a biomolecule, the method comprising:

(a) admixing any of the disclosed compounds with one or more biomolecules; and (b) detecting the compound by its visible properties.

Other embodiments provide a method for visually detecting an analyte, the method comprising:

(a) providing a compound as disclosed herein, wherein $R^2$ or $R^3$ comprises a linker comprising a covalent bond to a targeting moiety having specificity for the analyte;

(b) admixing the compound and the analyte, thereby associating the targeting moiety and the analyte; and (c) detecting the compound by its visible properties.

Other embodiments are directed to a composition comprising a compound of structure (I) and one or more analyte molecule, such as a biomolecule. Use of such composition in analytical methods for detection of the one or more biomolecules is also provided.

In some other different embodiments is provided a compound of structure (II):

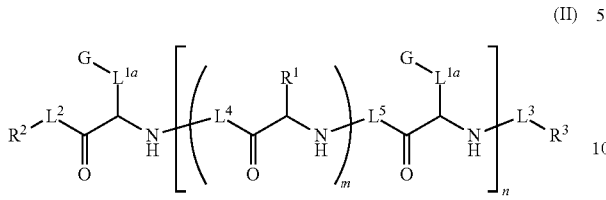

(II)

or a stereoisomer, salt or tautomer thereof, wherein $R^1$, $R^2$, $R^3$, $L^{1a}$, $L^2$, $L^3$, $L^4$, $L^5$, G, m and n are as defined herein. Compounds of structure (II) find utility in a number of applications, including use as intermediates for preparation of fluorescent and/or colored dyes of structure (I).

In yet other embodiments a method for labeling an analyte molecule is provided, the method comprising:

(a) admixing a compound of structure (II), wherein $R^2$ or $R^3$ is Q or a linker comprising a covalent bond to Q, with the analyte molecule;

(b) forming a conjugate of the compound and the analyte molecule; and (c) reacting the conjugate with a compound of formula $M\text{-}L^{1b}\text{-}G'$, thereby forming at least one covalent bond by reaction of G and G', wherein $R^2$, $R^3$, Q, G and $M\text{-}L^{1b}\text{-}G'$ are as defined herein.

In some different embodiments another method for labeling an analyte molecule is provided, the method comprising:

(a) admixing a compound of structure (II), wherein $R^2$ or $R^3$ is Q or a linker comprising a covalent bond to Q, with a compound of formula $M\text{-}L^{1b}\text{-}G'$, thereby forming at least one covalent bond by reaction of G and G; and (b) reacting the product of step (A) with the analyte molecule, thereby forming a conjugate of the product of step (A) and the analyte molecule wherein $R^2$, $R^3$, Q, G and $M\text{-}L^{1b}\text{-}G'$ are as defined herein.

In more different embodiments, a method for preparing a compound of structure (I) is provided, the method comprising admixing a compound of structure (II) with a compound of formula $M\text{-}L^{1b}\text{-}G'$, thereby forming at least one covalent bond by reaction of G and G', wherein G and $M\text{-}L^{1b}\text{-}G'$ are as defined herein.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ group.
"Carboxy" refers to the —$CO_2H$ group.
"Cyano" refers to the —CN group.
"Formyl" refers to the —C(=O)H group.
"Hydroxy" or "hydroxyl" refers to the —OH group.
"Imino" refers to the =NH group.
"Nitro" refers to the —$NO_2$ group.
"Oxo" refers to the =O substituent group.
"Sulfhydryl" refers to the —SH group.
"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —O$R_a$ where $R_a$ is an alkyl group as defined above containing one to twelve carbon atoms. Unless stated otherwise specifically in the specification, an alkoxy group is optionally substituted.

"Alkoxyalkylether" refers to a group of the formula —O$R_a R_b$ where $R_a$ is an alkylene group as defined above containing one to twelve carbon atoms, and Rb is an alkylether group as defined herein. Unless stated otherwise specifically in the specification, an alkoxyalkylether group is optionally substituted, for example substituted with an alcohol or —OP(=$R_a$)($R_b$)$R_c$, wherein:

$R_a$ is O or S;
$R_b$ is OH, SH, O$^-$, S$^-$, O$R_d$ or S$R_d$;
$R_c$ is OH, SH, O$^-$, S$^-$, O$R_d$, OL', S$R_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether; and
$R_d$ is a counter ion.

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom]$_x$-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —O$R_a$ where $R_a$ is a heteroalkyl group as defined above containing one to twelve carbon atoms. Unless stated otherwise specifically in the specification, a heteroalkoxy group is optionally substituted.

"Alkylaminyl" refers to a radical of the formula —NH$R_a$ or —N$R_a R_a$ where each $R_a$ is, independently, an alkyl radical as defined above containing one to twelve carbon atoms. Unless stated otherwise specifically in the specification, an alkylaminyl group is optionally substituted.

"Alkylcarbonyl" refers to a radical of the formula —(C=O)$R_a$ where $R_a$ is an alkyl radical as defined above containing one to twelve carbon atoms. Unless stated otherwise specifically in the specification, an alkylcarbonyl group is optionally substituted.

"Alkyloxycarbonyl" refers to a radical of the formula —(C=O)O$R_a$ where $R_a$ is an alkyl radical as defined above containing one to twelve carbon atoms. Unless stated otherwise specifically in the specification, an alkyloxycarbonyl group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]$_x$-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include amino acid and peptidyl linkers, ethylene oxide (e.g., polyethylene oxide) and the linking groups illustrated below:

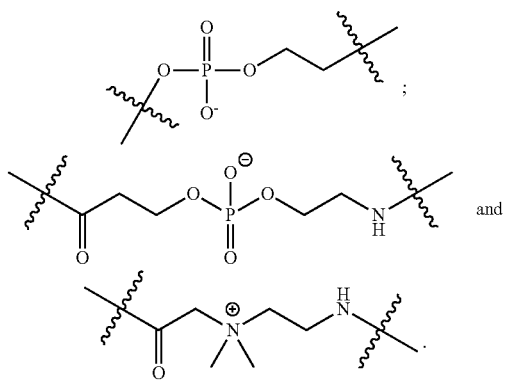

Multimers of the above linkers are included in various embodiments of heteroalkylene linkers.

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula —P(O$^-$)(=O)O— or —OP(O$^-$)(=O)O— and multimers and combinations thereof.

"Phosphate" refers to the —OP(=O)($R_a$)$R_b$ group, wherein $R_a$ is OH, O$^-$ or O$R_c$; and $R_b$ is OH, O$^-$, O$R_c$, a thiophosphate group or a further phosphate group, wherein $R_c$ is a counter ion (e.g., Na+ and the like).

"Phosphoalkyl" refers to the —OP(=O)($R_a$)$R_b$ group, wherein $R_a$ is OH, O$^-$ or O$R_c$; and $R_b$ is —Oalkyl, wherein $R_c$ is a counter ion (e.g., Na+ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined above.

"Phosphoalkylether" refers to the —OP(=O)($R_a$)$R_b$ group, wherein $R_a$ is OH, O$^-$ or O$R_c$; and $R_b$ is —Oalkylether, wherein $R_c$ is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined above.

"Thiophosphate" refers to the —OP(=$R_a$)($R_b$)$R_c$ group, wherein $R_a$ is O or S, $R_b$ is OH, O$^-$, S$^-$, O$R_d$ or S$R_d$; and $R_c$ is OH, SH, O$^-$, S$^-$, O$R_d$, S$R_d$, a phosphate group or a further thiophosphate group, wherein $R_d$ is a counter ion (e.g., Na+ and the like) and provided that: i) $R_a$ is S; ii) $R_b$ is S$^-$ or S$R_d$; iii)$R_c$ is SH, S$^-$ or S$R_d$; or iv) a combination of i), ii) and/or iii).

"Thiophosphoalkyl" refers to the —OP(=$R_a$)($R_b$)$R_c$ group, wherein $R_a$ is O or S, $R_b$ is OH, O$^-$, S$^-$, O$R_d$ or S$R_d$; and $R_c$ is —Oalkyl, wherein $R_d$ is a counter ion (e.g., Na+ and the like) and provided that: i) $R_a$ is S; ii) $R_b$ is S$^-$ or S$R_d$; or iii)$R_a$ is S and $R_b$ is S$^-$ or S$R_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined above.

"Thiophosphoalkylether" refers to the —OP(=$R_a$)($R_b$)$R_c$ group, wherein $R_a$ is O or S, $R_b$ is OH, O$^-$, S$^-$, O$R_d$ or S$R_d$; and $R_c$ is —Oalkylether, wherein $R_d$ is a counter ion (e.g., Na+ and the like) and provided that: i) $R_a$ is S; ii) $R_b$ is S$^-$ or S$R_d$; or iii)$R_a$ is S and $R_b$ is S$^-$ or S$R_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined above.

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptly, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, thiazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tetracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, alkoxyalkylether, heteroalkyl, heteroalkoxy, alkylaminyl, alkylcarbonyl, alkyloxycarbonyl, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In some embodiments, the optional substituent is $-OP(=R_a)(R_b)R_c$, wherein each of $R_a$, $R_b$ and $R_c$ is as defined for compounds of structure (I). In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1, 3-butadiene has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of embodiments of the invention (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive group (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The compounds of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of embodiments of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

A "solid support reside" refers to the functional group remaining attached to a molecule when the molecule is cleaved from the solid support. Solid support residues are known in the art and can be easily derived based on the structure of the solid support and the group linking the molecule thereto.

A "targeting moiety" is a moiety that selectively binds or associates with a particular target, such as an analyte molecule. "Selectively" binding or associating means a targeting moiety preferentially associates or binds with the desired target relative to other targets. In some embodiments the compounds disclosed herein include linkages to targeting moieties for the purpose of selectively binding or associating the compound with an analyte of interest (i.e., the target of the targeting moiety), thus allowing detection of the analyte. Exemplary targeting moieties include, but are not limited to, antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for detection of cells of interest. Small molecules that selectively bind or associate with a desired analyte are also contemplated as targeting moieties in certain embodiments. One of skill in the art will understand other analytes, and the corresponding targeting moiety, that will be useful in various embodiments.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the invention disclosed herein are also meant to encompass all compounds of structure (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

Isotopically-labeled compounds of structure (I) or (II) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic or organic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the compounds of the invention (e.g., compounds of structure I or II), or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

An "amino acid side chain" or "side chain" refers to substituents attached to the α-carbon, β-carbon, or γ-carbon of an amino acid. Amino acid side chains can be those associated with natural or unnatural amino acids.

An "amino acid sequence" or "peptide sequence" refers to the primary structure of linked amino acid residues along a backbone formed via peptide bonds. Sequences are generally denoted from the N-terminal end to the C-terminal end. Embodiments of the present invention include compounds comprising certain amino acid sequences where indicated. Amino acid sequences are indicated, where appropriate, by 3-letter or 1-letter abbreviations.

A "letter code," "1-letter code," or "3-letter code" refers to an indication or abbreviation for an amino acid or amino acid residue in an amino acid sequence. A general list of 1 and 3-letter codes and the amino acid they correspond to is found below:

| Amino Acid | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Selenocysteine | Sec | U |
| Pyrrolysine | Pyl | O |

A "beta sheet," "β-sheet," "beta pleated sheet," or "β-pleated sheet" refers to secondary structure of amino acid sequences that forms via intra molecular folding. Strands of amino acids are connected laterally by hydrogen bonding forming a generally twisted, pleated sheet. Strands of amino acids that form this secondary structure are generally 3 to 10 amino acid residues in length. The present invention includes amino acid sequences that include amino acid residues with beta sheet forming propensities where beta sheet moieties are indicated. These residues include, but are not limited to, glycine, methionine, serine, valine, tyrosine, phenylalanine, tryptophan, threonine, and isoleucine.

An "alpha helix" or "α-helix" refers to secondary structure of amino acid chains that forms via intra molecular folding. A spiral conformation is formed wherein backbone N—H groups donate a hydrogen bond to backbone C═O groups of the amino acid four residues earlier. Amino acid side chain sequence influences formation of alpha helical structure. The present invention includes amino acid sequences that include residues with helix-forming propensities where alpha helix moieties are indicated. These residues include, but are not limited to, glycine, methionine, alanine, arginine, histidine, leucine, glutamate, glutamic acid, phenylalanine, valine, tyrosine, and lysine.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, compounds useful as fluorescent and/or colored dyes in various analytical methods are provided. In general terms, embodiments of the present invention are directed to dimers and higher polymers of fluorescent and/or colored moieties. The fluorescent and or colored moieties are linked by linkers having amino acid or other monomer units optionally with specific secondary structures or multiple positively or negatively charged moieties at the pH at which an assay is conducted. Without wishing to be bound by theory, it is believed the length and specific characteristics (e.g. secondary structure, positive charge, etc.) of the linker helps to maintain sufficient spatial distance between the fluorescent and/or colored moieties such that intramolecular quenching is reduced or eliminated, this resulting in a dye compound having a high molar "brightness" (e.g., high fluorescence emission).

For example, the linker may comprise carboxylate, phosphate and/or thiophosphate moieties when a negative charge is desired. When positive charges are desired, linking groups containing primary or quaternary amine groups and/or other groups capable of holding a positive charge may be used. When a specific secondary structure is desired, linking groups with an amino acid sequence amenable to such a structure (e.g., alpha-helix or beta sheet) may be used. By "charged moieties" it is understood that the moieties will be charged at certain pH's, for example at the pH at which an assay employing the compound is performed, but it is not a requirement that the "charged moieties" be charged at all pH's.

Accordingly, in some embodiments the compounds have the following structure (A):

wherein L is, at each occurrence, independently a linker comprising at least one amino acid, for example a linker comprising a peptide, M is, at each occurrence, independently as defined herein for structure (I), n is an integer of 1 or greater and T is absent, a terminal group or a bond to L.

In other embodiments is provided a compound having the following structure (I):

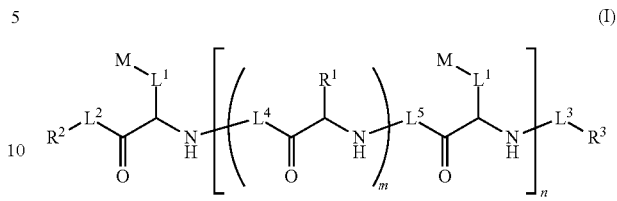

or a stereoisomer, salt or tautomer thereof, wherein:

M is, at each occurrence, independently a moiety comprising two or more carbon-carbon double bonds and at least one degree of conjugation;

$L^1$ is at each occurrence, independently either: i) an optional alkylene, alkenylene, alkynylene, heteroalkylene, heteroalkenylene or heteroalkynylene linker; or ii) a linker comprising a functional group capable of formation by reaction of two complementary reactive groups;

$L^2$, $L^3$, $L^4$ and $L^5$ are, at each occurrence, independently optional alkylene, alkenylene, alkynylene, heteroalkylene, heteroalkenylene or heteroalkynylene linkers;

$R^1$ is, at each occurrence, independently a natural or unnatural amino acid side chain;

$R^2$ and $R^3$ are each independently H, —OH, —SH, —NH$_2$, —CO$_2$H, alkyl, alkylether, alkoxy, heteroalkyl, alkylaminyl, alkylcarbonyl, alkyloxycarbonyl, Q, a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue or a linker comprising a covalent bond to a further compound of structure (I), wherein the alkyl, alkylether, alkylaminyl, alkylcarbonyl and alkyloxycarbonyl are optionally substituted with hydroxyl, amino, sulfhydryl, phosphate, thiophosphate, phosphoalkyl, thiophosphoalkyl, phosphoalkylether or thiophosphoalkylether, or combinations thereof; Q is, at each occurrence, independently a moiety comprising a reactive group capable of forming a covalent bond with an analyte molecule, a solid support or a complementary reactive group Q;

m is, at each occurrence, independently an integer of zero or greater; and n is an integer of one or greater.

In other embodiments of structure (I):

M is, at each occurrence, independently a moiety comprising two or more carbon-carbon double bonds and at least one degree of conjugation;

$L^1$ is at each occurrence, independently either: i) an optional alkylene, alkenylene, alkynylene, heteroalkylene, heteroalkenylene or heteroalkynylene linker; or ii) a linker comprising a functional group capable of formation by reaction of two complementary reactive groups;

$L^2$, $L^3$, $L^4$ and $L^5$ are, at each occurrence, independently optional alkylene, alkenylene, alkynylene, heteroalkylene, heteroalkenylene or heteroalkynylene linkers;

$R^1$ is, at each occurrence, independently a natural or unnatural amino acid side chain;

$R^2$ and $R^3$ are each independently H, —OH, —SH, —NH$_2$, —CO$_2$H, alkyl, alkylether, alkylaminyl, alkylcarbonyl, alkyloxycarbonyl, Q, a linker comprising a covalent bond to Q, a linker comprising a covalent bond to an analyte molecule, a linker comprising a covalent bond to a solid support or a linker comprising a covalent bond to a further compound of structure (I), wherein the alkyl, alkylether, alkylaminyl, alkylcarbonyl and alkyloxycarbonyl are optionally substituted with hydroxyl, amino, sulfhydryl, phosphate, thiophosphate, phosphoalkyl, thiophosphoalkyl, phosphoalkylether or thiophosphoalkylether, or combinations thereof;

Q is, at each occurrence, independently a moiety comprising a reactive group capable of forming a covalent bond with an analyte molecule, a solid support or a complementary reactive group Q;

m is, at each occurrence, independently an integer of zero or greater; and n is an integer of one or greater.

The various linkers and substituents (e.g., M, Q, $R^1$, $R^2$, $R^3$, $L^1$, $L^2$, $L^3$, $L^4$ and $L^5$) in the compound of structure (I) are optionally substituted with one more substituent. For example, in some embodiments the optional substituent is selected to optimize the water solubility or other property of the compound of structure (I). In certain embodiments, each alkyl, alkoxy, alkylether, alkoxyalkylether, phosphoalkyl, thiophosphoalkyl, phosphoalkylether and thiophosphoalkylether in the compound of structure (I) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether.

In some embodiments, at least one $R^1$ is a neutral amino acid side chain, for example H or alkyl.

In other embodiments, at least one $R^1$ is a charged amino acid side chain, for example a side chain comprising an amidinyl, guanidinyl or imidazolyl group.

In other embodiments, $R^1$ is, at each occurrence, independently H, alkyl, $-CH_2CO_2^-$, $-CH_2CH_2CO_2^-$, $-CH_2CH_2CH_2CH_2NH_3^+$, $-CH_2CH_2CH_2NHC(-NH_2^+)NH_2$ or imidazolyl.

In various other embodiments, $R^1$, $L^4$ and m are selected such that

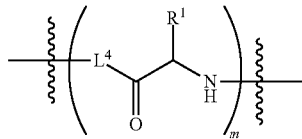

has an amino acid sequence of $(G)_{10}$, (GDGDGDGDGD) or (GKGKGKGKGK).

In different embodiments, $R^1$, $L^4$ and m are selected such that

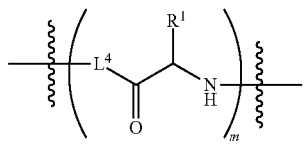

has an amino acid sequence capable of forming an α-helix or β-sheet secondary structure. For example, in some embodiments the amino acid sequence is (GGEEFMLVYK-FARKHGG) or (GGMSMVVSGG).

In different embodiments, $L^4$ and $L^5$ are absent at each occurrence. In other embodiments, $L^4$ or $L^5$, or both, is present for at least one occurrence. For example, in some embodiments, when present, $L^4$ or $L^5$, or both, is a heteroalkylene linker.

$L^4$ and/or $L^5$ can include charged moieties. For example, in some embodiments, $L^4$ and/or $L^5$ is a heteroalkylene linker comprising a functional group capable of maintaining a positive or negative charge at pH values ranging from 3 to 11 in aqueous solution. in some embodiments, $L^4$ and/or $L^5$ is a heteroalkylene linker comprising a functional group capable of maintaining a positive charge at pH values ranging from 3 to 11 in aqueous solution. in some embodiments, $L^4$ and/or $L^5$ is a heteroalkylene linker comprising a functional group capable of maintaining a negative charge at pH values ranging from 3 to 11 in aqueous solution.

In some embodiments, at least one occurrence of $L^4$ or $L^5$, or both, has the following structure:

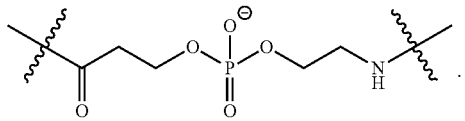 [SMILES: *NCCOP(=O)([O-])OCCC(*)=O]

In other embodiments, at least one occurrence of $L^4$ or $L^5$, or both, has the following structure:

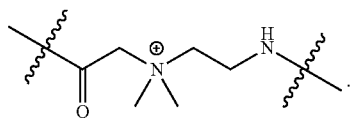 [SMILES: *NCC[N+](C)(C)CC(*)=O]

The optional linker $L^1$ can be used as a point of attachment of the M moiety to the remainder of the compound. For example, in some embodiments a synthetic precursor to the compound of structure (I) is prepared, and the M moiety is attached to the synthetic precursor using any number of facile methods known in the art, for example methods referred to as "click chemistry." For this purpose any reaction which is rapid and substantially irreversible can be used to attach M to the synthetic precursor to form a compound of structure (I). Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom. In some embodiments the reaction to form $L^1$ may be performed in an aqueous environment.

Accordingly, in some embodiments $L^1$ is at each occurrence a linker comprising a functional group capable of formation by reaction of two complementary reactive groups, for example a functional group which is the product of one of the foregoing "click" reactions. In various embodiments, for at least one occurrence of $L^1$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group with a complementary reactive group.

In other embodiments, for at least one occurrence of $L^1$, the functional group can be formed by reaction of an alkyne and an azide.

In more embodiments, for at least one occurrence of $L^1$, the functional group comprises an alkene, ester, amide, thioester, disulfide, carbocyclic, heterocyclic or heteroaryl group. In some more specific embodiments, for at least one occurrence of $L^1$, $L^1$ is a linker comprising a triazolyl functional group.

In still other embodiments, for at least one occurrence of $L^1$, $L^1$-M has the following structure:

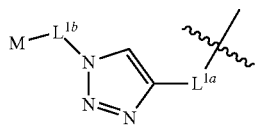

wherein $L^{1a}$ and $L^{1b}$ are each independently optional linkers.

In different embodiments, for at least one occurrence of $L^1$, $L^1$-M has the following structure:

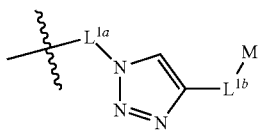

wherein $L^{1a}$ and $L^{1b}$ are each independently optional linkers.

In various embodiments of the foregoing, $L^{1a}$ or $L^{1b}$, or both, is absent. In other embodiments, $L^{1a}$ or $L^{1b}$, or both, is present.

In some embodiments $L^{1a}$ and $L^{1b}$, when present, are each independently alkylene or heteroalkylene.

In still other different embodiments of structure (I), $L^1$ is at each occurrence, independently an optional alkylene or heteroalkylene linker.

In more embodiments, $L^2$ and $L^3$ are, at each occurrence, independently are independently absent or a heteroalkylene linker. For example, in some embodiments the heteroalkylene linker is an amino acid or peptidyl linker.

In other various embodiments, $R^2$ is —$NH_2$. In other embodiments, $R^3$ is Q, a linker comprising a covalent bond to Q or a linker comprising a covalent bond to a solid support.

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (I) (e.g., in the $R^2$ or $R^3$ position), and Q and Q' comprise complementary reactive groups such that reaction of the compound of structure (I) and the further compound of structure (I) results in covalently bound dimer of the compound of structure (I). Multimer compounds of structure (I) can also be prepared in an analogous manner and are included within the scope of embodiments of the invention.

The type of Q group and connectivity of the Q group to the remainder of the compound of structure (I) is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (I) comprise Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for conjugation with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (I). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

In other embodiments, the Q moiety is conveniently masked (e.g., protected) as a disulfide moiety, which can later be reduced to provide an activated Q moiety for binding to a desired analyte molecule or targeting moiety. For example, the Q moiety may be masked as a disulfide having the following structure:

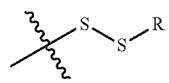

wherein R is an optionally substituted alkyl group. For example, in some embodiments, Q is provided as a disulfide moiety having the following structure:

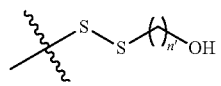

where n is an integer from 1 to 10, for example 6.

Exemplary Q moieties are provided in Table I below.

TABLE 1

| Exemplary Q Moieties | |
|---|---|
| Structure | Class |
| —SH | Sulfhydryl |
| —N=C=S | Isothiocyanate |
| (methyl imidoester with NH₂⁺Cl⁻) | Imidoester |
| (acyl azide structure) | Acyl Azide |
| (tetrafluorophenyl ester) | Activated Ester |
| (pentafluorophenyl ester) | Activated Ester |
| (sulfo-nitrophenyl ester) | Activated Ester |
| (thiosuccinimidyl sulfo-nitrophenyl ester) | Activated Ester |
| (NHS ester) | Activated Ester |

TABLE 1-continued

| Exemplary Q Moieties | |
|---|---|
| Structure | Class |
| (sulfo-NHS ester) | Activated Ester |
| —S(O)₂—X, X = halo | Sulfonyl halide |
| (maleimide) | Maleimide |
| (thiosuccinimide-ethyl-maleimide) | Maleimide |
| (cyclohexane carboxamide maleimide, SMCC-type) | Maleimide |
| —NH—C(O)—CH₂—X, X = halo | α-haloimide |
| (pyridyl disulfide) | Disulfide |
| (methyl ester with PPh₂, Staudinger phosphine) | Phosphine |
| —N₃ | Azide |

TABLE 1-continued

Exemplary Q Moieties

| Structure | Class |
|---|---|
| (alkyne structure) | Alkyne |
| (biotin structure) | Biotin |
| (diene structure) | Diene |
| (alkene structure) | Alkene/dienophile |
| (alkene with EWG structure) EWG = electron withdrawing group | Alkene/dienophile |
| —NH$_2$ | Amino |

It should be noted that in some embodiments, wherein Q is SH, the SH moiety will tend to form disulfide bonds with another sulfhydryl group on another compounds of structure (I). Accordingly, some embodiments include compounds of structure (I), which are in the form of disulfide dimers, the disulfide bond being derived from SH Q groups.

In certain embodiments, one of $R^2$ or $R^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In different embodiments, the solid support is a polymeric bead or nonpolymeric bead.

The value of m is another variable that can be selected based on the desired fluorescence and/or color intensity. In some embodiments, m is, at each occurrence, independently an integer from 1 to 20. For example, in some embodiments m is, at each occurrence, independently an integer from 1 to 10, such as 1, 2, 3, 4 or 5. In some embodiments, m is 1. In some embodiments, m is 2. In some embodiments, m is 3. In some embodiments, m is 4. In some embodiments, m is 5.

The fluorescence intensity can also be tuned by selection of different values of n. In certain embodiments, n is an integer from 1 to 100. For example, in some embodiments, n is an integer from 1 to 10. In some embodiments, n is 1.

In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

M is selected based on the desired optical properties, for example based on a desired color and/or fluorescence emission wavelength. In some embodiments, M is the same at each occurrence; however, it is important to note that each occurrence of M need not be an identical M, and certain embodiments include compounds wherein M is not the same at each occurrence. For example, in some embodiments each M is not the same and the different M moieties are selected to have absorbance and/or emissions for use in fluorescence resonance energy transfer (FRET) methods. For example, in such embodiments the different M moieties are selected such that absorbance of radiation at one wavelength causes emission of radiation at a different wavelength by a FRET mechanism. Exemplary M moieties can be appropriately selected by one of ordinary skill in the art based on the desired end use. Exemplary M moieties for FRET methods include fluorescein and 5-TAMRA (5-carboxytetramethylrhodamine, succinimidyl ester) dyes.

M may be attached to the remainder of the molecule from any position (i.e., atom) on M. One of skill in the art will recognize means for attaching M to the remainder of molecule. Exemplary methods include the "click" reactions described herein.

In some embodiments, M is a fluorescent or colored moiety. Any fluorescent and/or colored moiety may be used, for examples those known in the art and typically employed in colorimetric, UV, and/or fluorescent assays may be used. Examples of M moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and ALEXA FLOUR® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings.

In some embodiments, M is cyclic. For example, in some embodiments M is carbocyclic. In other embodiment, M is heterocyclic. In still other embodiments of the foregoing, M, at each occurrence, independently comprises an aryl moiety.

In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (I) or (IA), M, at each occurrence, independently comprises at least one heteroatom. For example, in some embodiments, the heteroatom is nitrogen, oxygen or sulfur.

In still more embodiments of any of the foregoing, M, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, M is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is, at each occurrence, independently a coumarin dye, resorufin dye, dipyrromethaneboron difluoride dye, ruthenium bipyridyl dye, energy transfer dye, thiazole orange dye, polymethine or N-aryl-1,8-naphthalimide dye.

In still more embodiments of any of the foregoing, M at each occurrence is the same. In other embodiments, each M is different. In still more embodiments, one or more M is the same and one or more M is different.

In some embodiments, M is pyrene, perylene, perylene monoimide or 6-FAM or derivative thereof. In some other embodiments, M has one of the following structures:

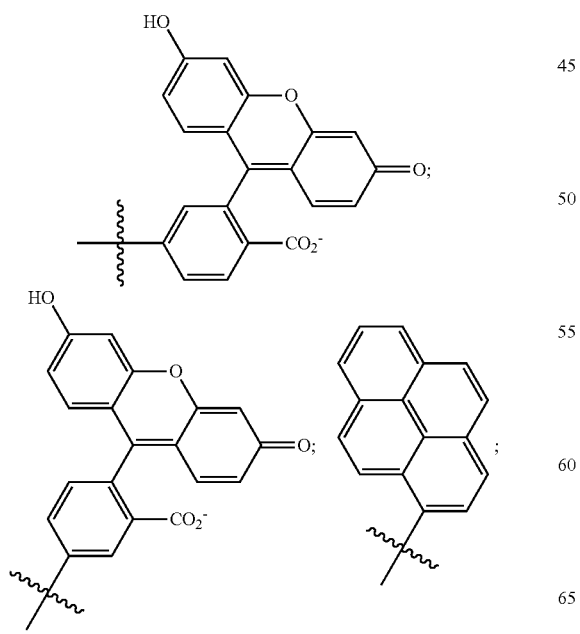

-continued

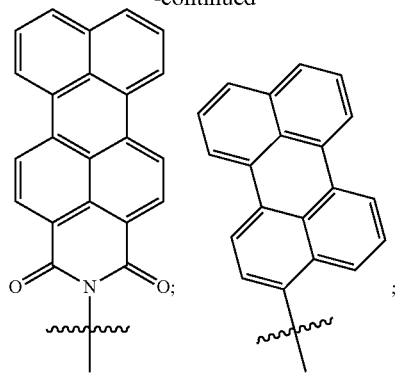

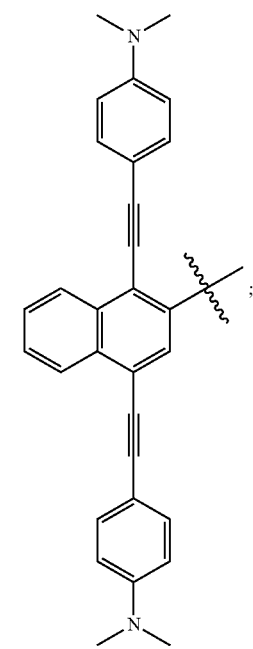

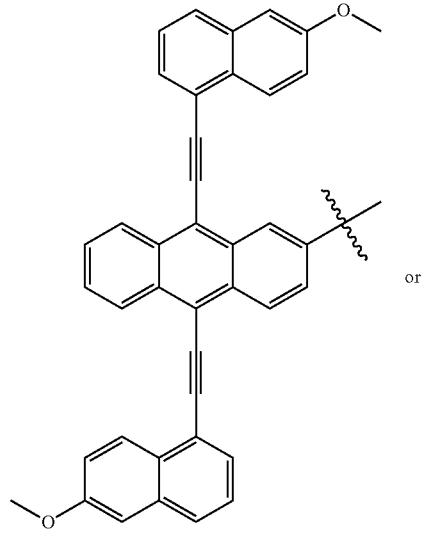

or

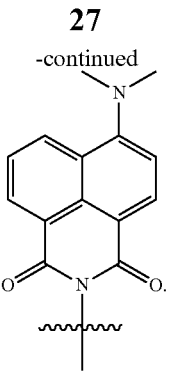

Although M moieties comprising carboxylic acid groups are depicted in the anionic form ($CO_2^-$) above, one of skill in the art will understand that this will vary depending on pH, and the protonated form ($CO_2H$) is included in various embodiments.

In some specific embodiments, the compound of structure (I) is a compound selected from Table 2. The compounds in Table 2 were prepared according to the procedures set forth in the Examples and their identity confirmed by mass spectrometry.

TABLE 2

Exemplary Compounds of Structure I

| # | Structure |
|---|---|
| I-1 | 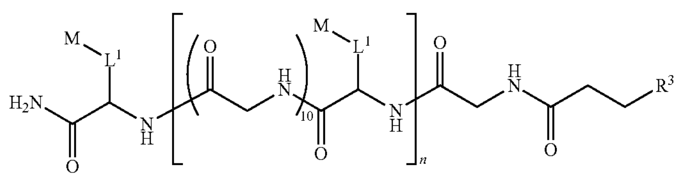 |
| I-2 | 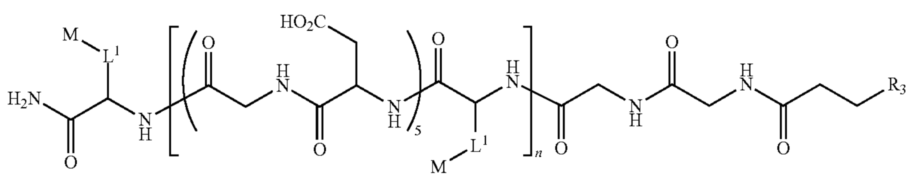 |
| I-3 | 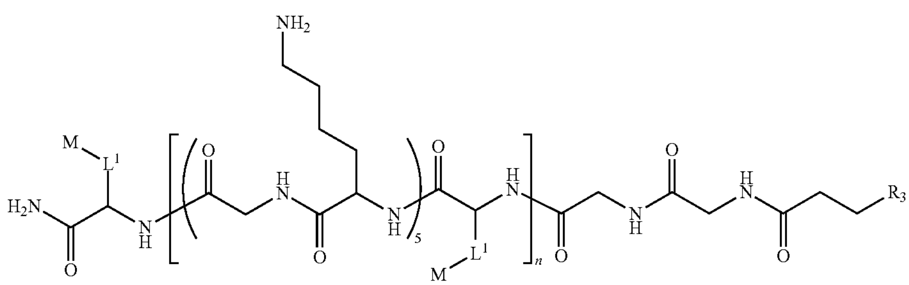 |
| I-4 | 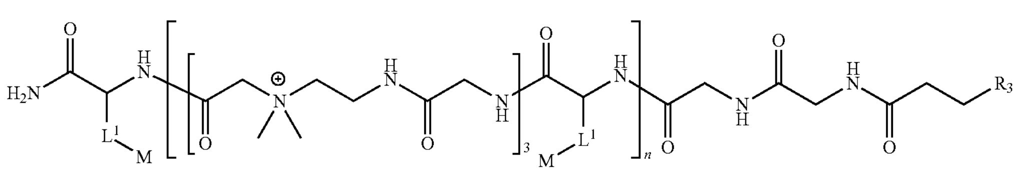 |

TABLE 2-continued

Exemplary Compounds of Structure I

| # | Structure |
|---|-----------|
| I-5 | 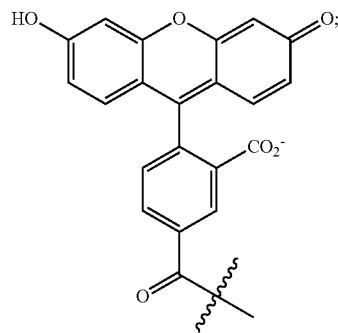 |
| I-6 | 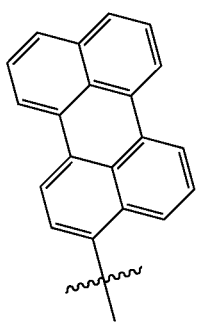 |
| I-7 | (structure with H₂N-[GGMSMVVSGG]-...) |

As used in Table 2 at entries 1-6 and 1-7, and where indicated throughout the application, letter sequences incorporated in structural drawings indicate amino acid sequences denoted by 1-letter codes.

In certain embodiments of the compounds in Table 2, M is a fluorescein, perylene or pyrene moiety having the following structures (F', E' or Y'):

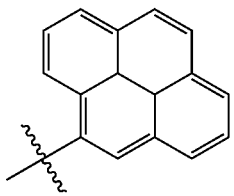

The presently disclosed dye compounds are "tunable," meaning that by proper selection of the variables in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Although all variables may have an effect on the molar fluorescence of the compounds, proper selection of M, m, n, $L^4$ and $L^5$ is believed to play an important role in the molar fluorescence of the compounds. Accordingly, in one embodiment is provided a method for obtaining a compound having a desired molar fluorescence, the method comprising selecting an M moiety having a known fluorescence, preparing a compound of structure (I) comprising the M, and selecting the appropriate variables for m, n, $L^4$ and $L^5$ to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9× 10× or even higher relative to the parent fluorophore. Various embodiments include preparing compounds having the desired fold increase in fluorescence relative to the parent fluorophore by proper selection of m, n, $L^4$ and $L^5$.

For ease of illustration, various compounds comprising phosphorous moieties (e.g., phosphate and the like) are depicted in the anionic state (e.g., —OPO(OH)O⁻, —OPO$_3^{2-}$). One of skill in the art will readily understand that the charge is dependent on pH and the uncharged (e.g., protonated or salt, such as sodium or other cation) forms are also included in the scope of the invention.

Compositions comprising any of the foregoing compounds and one or more analyte molecules (e.g., biomolecules) are provided in various other embodiments. In some embodiments, use of such compositions in analytical methods for detection of the one or more analyte molecules is also provided.

In still other embodiments, the compounds are useful in various analytical methods. For example, in certain embodiments the disclosure provides a method of staining a sample, the method comprising adding to said sample a compound of structure (I) in an amount sufficient to produce an optical response when said sample is illuminated at an appropriate wavelength. In some embodiments of the foregoing methods, $R^2$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^2$ is a linker comprising a covalent linkage to a solid support such as a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:
  (a) providing the compound of structure (I), wherein $R^2$ or $R^3$ is a linker comprising a covalent bond to the analyte molecule; and
  (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:
  (a) admixing any of the foregoing compounds with one or more analyte molecules; and
  (b) detecting the compound by its visible properties.

In other embodiments is provided a method for visually detecting an analyte molecule, the method comprising:
  (a) admixing the compound of structure (I), wherein $R^2$ or $R^3$ is Q or a linker comprising a covalent bond to Q, with the analyte molecule;
  (b) forming a conjugate of the compound and the analyte molecule; and
  (c) detecting the conjugate by its visible properties.

Other exemplary methods include a method for detecting an analyte, the method comprising:
  (a) providing a compound of structure (I), wherein $R^2$ or $R^3$ comprises a linker comprising a covalent bond to a targeting moiety having specificity for the analyte;
  (b) admixing the compound and the analyte, thereby associating the targeting moiety and the analyte; and
  (c) detecting the compound, for example by its visible or fluorescent properties.

In certain embodiments of the foregoing method, the analyte is a particle, such as a cell, and the method includes use of flow cytometry. For example, the compound may be provided with a targeting moiety, such as an antibody, for selectively associating with the desired cell, thus rendering the cell detectable by any number of techniques, such as visible or fluorescence detection. Appropriate antibodies can be selected by one of ordinary skill in the art depending on the desired end use. Exemplary antibodies for use in certain embodiments include UCHT1 and MOPC-21.

Embodiments of the present compounds thus find utility in any number of methods, including, but not limited: cell counting; cell sorting; biomarker detection; quantifying apoptosis; determining cell viability; identifying cell surface antigens; determining total DNA and/or RNA content; identifying specific nucleic acid sequences (e.g., as a nucleic acid probe); and diagnosing diseases, such as blood cancers.

In some other different embodiments, the compounds of structure (I) can be used in various for analysis of cells. For example, by use of flow cytometry, the compounds can be used to discriminate between live and dead cells, evaluate the health of cells (e.g., necrosis vs. early apoptitic vs. late apoptitic vs. live cell), tracking ploidy and mitosis during the cell cycle and determining various states of cell proliferation. While not wishing to be bound by theory, it is believed that embodiments of the compounds of structure (I) preferentially bind to positively charged moieties. Accordingly, in some embodiments the compounds include positively charged moieties (e.g., in the linker $L^4$ or $L^5$) and may be used in methods for determining the presence of non-intact cells, for example necrotic cells. For example, the presence of necrotic cells can be determined by admixing a sample containing cells with a compound of structure (I) and analyzing the mixture by flow cytometry. The compound of structure (I) binds to necrotic cells, and thus their presence is detectable under flow cytometry conditions. In contrast to other staining reagents which require an amine reactive group to bind to necrotic cells, embodiments of the staining methods of employing compounds of structure (I) do not require a protein-free incubation buffer, and thus the methods are more efficient to perform than related known methods.

In various other embodiments, the compounds can be used in related methods for determine the presence of positively charged moieties in intact or non-intact cells, apoptitic bodies, depolarized membranes and/or permealized membranes.

In addition to the above methods, embodiments of the compounds of structure (I) find utility in various disciplines and methods, including but not limited to: imaging in endoscopy procedures for identification of cancerous and other tissues; single-cell and/or single molecule analytical methods, for example detection of polynucleotides with little or no amplification; cancer imaging, for example by including a targeting moiety, such as an antibody or sugar or other moiety that preferentially binds cancer cells, in a compound of structure (I) to; imaging in surgical procedures; binding of histones for identification of various diseases; drug delivery, for example by replacing the M moiety in a compound of structure (I) with an active drug moiety; and/or contrast agents in dental work and other procedures, for example by preferential binding of the compound of structure (I) to various flora and/or organisms.

In various other embodiments, compounds useful for preparation of the compound of structure (I) are provided. The compounds can be prepared as described herein and then the M moiety covalently attached to the compound via any number of synthetic methodologies (e.g., the "click" reactions described above) to form a compound of structure (I). Accordingly, in various embodiments a compound is provided having the following structure (II):

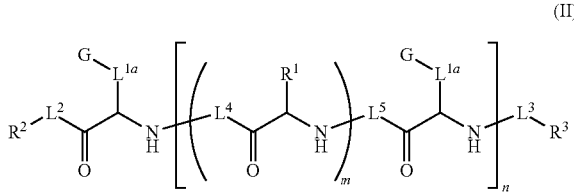

(II)

or a stereoisomer, salt or tautomer thereof, wherein:

G is, at each occurrence, independently a moiety comprising a reactive group capable of forming a covalent bond with a complementary reactive group;

$L^{1a}$, $L^2$, $L^3$, $L^4$ and $L^5$ are, at each occurrence, independently an optional alkylene, alkenylene, alkynylene, heteroalkylene, heteroalkenylene or heteroalkynylene linker;

$R^1$ is, at each occurrence, independently a natural or unnatural amino acid side chain;

$R^2$ and $R^3$ are each independently H, —OH, —SH, —$NH_2$, —$CO_2H$, alkyl, alkylether, alkoxy, heteroalkyl, alkylaminyl, alkylcarbonyl, alkyloxycarbonyl, Q, a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue or a linker comprising a covalent bond to a further compound of structure (I), wherein the alkyl, alkylether, alkylaminyl, alkylcarbonyl and alkyloxycarbonyl are optionally substituted with hydroxyl, amino, sulfhydryl, phosphate, thiophosphate, phosphoalkyl, thiophosphoalkyl, phosphoalkylether or thiophosphoalkylether, or combinations thereof;

Q is, at each occurrence, independently a moiety comprising a reactive group capable of forming a covalent bond with an analyte molecule, a solid support or a complementary reactive group Q;

m is, at each occurrence, independently an integer of zero or greater; and n is an integer of one or greater.

In other embodiments of structure (II): G is, at each occurrence, independently a moiety comprising a reactive group capable of forming a covalent bond with a complementary reactive group;

$L^{1a}$, $L^2$, $L^3$, $L^4$ and $L^5$ are, at each occurrence, independently an optional alkylene, alkenylene, alkynylene, heteroalkylene, heteroalkenylene or heteroalkynylene linker;

$R^1$ is, at each occurrence, independently a natural or unnatural amino acid side chain;

$R^2$ and $R^3$ are each independently H, —OH, —SH, —$NH_2$, —$CO_2H$, alkyl, alkylether, alkylaminyl, alkylcarbonyl, alkyloxycarbonyl, Q, a linker comprising a covalent bond to Q, a linker comprising a covalent bond to an analyte molecule, a linker comprising a covalent bond to a solid support or a linker comprising a covalent bond to a further compound of structure (I), wherein the alkyl, alkylether, alkylaminyl, alkylcarbonyl and alkyloxycarbonyl are optionally substituted with hydroxyl, amino, sulfhydryl, phosphate, thiophosphate, phosphoalkyl, thiophosphoalkyl, phosphoalkylether or thiophosphoalkylether, or combinations thereof;

Q is, at each occurrence, independently a moiety comprising a reactive group capable of forming a covalent bond with an analyte molecule, a solid support or a complementary reactive group Q;

m is, at each occurrence, independently an integer of zero or greater; and n is an integer of one or greater.

The G moiety in the compound of structure (II) can be selected from any moiety comprising a group having the appropriate reactivity group for forming a covalent bond with a complementary group on an M moiety. In exemplary embodiments, the G moiety can be selected from any of the Q moieties described herein, including those specific examples provided in Table 1. In some embodiments, G comprises, at each occurrence, independently a moiety suitable for reactions including: the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom.

In some embodiments, G is, at each occurrence, independently a moiety comprising an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group.

In other embodiments, G comprises, at each occurrence, independently an alkyne or an azide group. In different embodiments, G comprises, at each occurrence, independently a reactive group capable of forming a functional group comprising an alkene, ester, amide, thioester, disulfide, carbocyclic, heterocyclic or heteroaryl group, upon reaction with the complementary reactive group. For example, in some embodiment the heteroaryl is triazolyl.

In other embodiments of structure (II), each $L^{1a}$ is absent. In other embodiments, each $L^{1a}$ is present, for example $L^{1a}$ is, at each occurrence, independently heteroalkylene.

In other of any of the foregoing embodiments of compound (II), G is, at each occurrence, independently

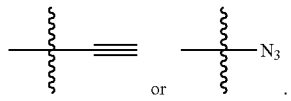

In some embodiments of structure (II), at least one $R^1$ is a neutral amino acid side chain, for example H or alkyl.

In other embodiments of structure (II), at least one $R^1$ is a charged amino acid side chain, for example a side chain comprising an amidinyl, guanidinyl or imidazolyl group.

In other embodiments of structure (II), $R^1$ is, at each occurrence, independently H, alkyl, —$CH_2CO_2^-$, —$CH_2CH_2CO_2^-$, —$CH_2CH_2CH_2CH_2NH_3^+$, —$CH_2CH_2CH_2NHC(=NH_2^+)NH_2$ or imidazolyl.

In various other embodiments of structure (II), $R^1$, $L^4$ and m are selected such that

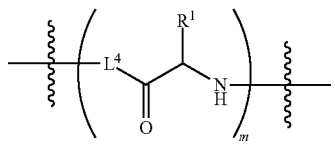

has an amino acid sequence of $(G)_{10}$, (GDGDGDGDGD) or (GKGKGKGKGK).

In different embodiments of structure (II), $R^1$, $L^4$ and m are selected such that

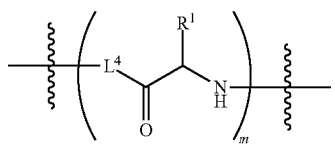

has an amino acid sequence capable of forming an α-helix or β-sheet secondary structure. For example, in some embodiments the amino acid sequence is (GGEEFMLVYK-FARKHGG) or (GGMSMVVSGG).

In different embodiments of structure (II), $L^4$ and $L^5$ are absent at each occurrence. In other embodiments, $L^4$ or $L^5$, or both, is present for at least one occurrence. For example, in some embodiments, when present, $L^4$ or $L^5$, or both, is a heteroalkylene linker.

$L^4$ and/or $L^5$ can include charged moieties. For example, in some embodiments, $L^4$ and/or $L^5$ is a heteroalkylene linker comprising a functional group capable of maintaining a positive or negative charge at pH values ranging from 3 to 11 in aqueous solution. in some embodiments, $L^4$ and/or $L^5$ is a heteroalkylene linker comprising a functional group capable of maintaining a positive charge at pH values ranging from 3 to 11 in aqueous solution. in some embodiments, $L^4$ and/or $L^5$ is a heteroalkylene linker comprising a functional group capable of maintaining a negative charge at pH values ranging from 3 to 11 in aqueous solution.

In some embodiments of structure (II), at least one occurrence of $L^4$ or $L^5$, or both, has the following structure:

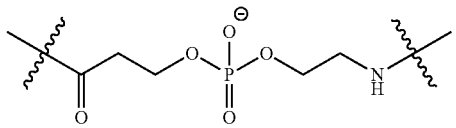

In other embodiments of structure (II), at least one occurrence of $L^4$ or $L^5$, or both, has the following structure:

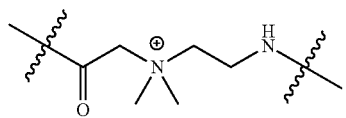

In more embodiments of structure (II), $L^2$ and $L^3$ are, at each occurrence, independently are independently absent or a heteroalkylene linker. For example, in some embodiments the heteroalkylene linker is an amino acid or peptidyl linker.

In other various embodiments of structure (II), $R^2$ is —$NH_2$. In other embodiments, $R^3$ is Q, a linker comprising a covalent bond to Q or a linker comprising a covalent bond to a solid support.

In still other embodiments of compounds of structure (II), Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (II) (e.g., in the $R^2$ or $R^3$ position), and Q and Q' comprise complementary reactive groups such that reaction of the compound of structure (II) and the further compound of structure (II) results in covalently bound dimer of the compound of structure (II). Multimer compounds of structure (II) can also be prepared in an analogous manner and are included within the scope of embodiments of the invention.

The type of Q group and connectivity of the Q group to the remainder of the compound of structure (II) is not limited, provided that Q comprises a moiety having appropriate reactivity for forming the desired bond.

In certain embodiments of compounds of structure (II), the Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (II) comprises Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

Exemplary Q moieties for compounds of structure (II) are provided in Table I above.

As with compounds of structure (I), in some embodiments of compounds of structure (II), wherein Q is SH, the SH moiety will tend to form disulfide bonds with another sulfhydryl group on another compound of structure (II). Accordingly, some embodiments include compounds of structure (II), which are in the form of disulfide dimers, the disulfide bond being derived from SH Q groups.

In some other embodiments of compounds of structure (II), one of $R^2$ or $R^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

In other embodiments of compounds of structure (II), m is, at each occurrence, independently an integer from 1 to 20. For example, in some embodiments m is, at each occurrence, independently an integer from 1 to 10, such as 1, 2, 3 or 5. In some embodiments, m is 1. In some embodiments, m is 2. In some embodiments, m is 3. In some embodiments, m is 4. In some embodiments, m is 5.

In yet different embodiments of compounds of structure (II), n is an integer from 1 to 100. For example, in some embodiments, n is an integer from 1 to 10. In some embodiments, n is 1. In some embodiments, n is 2. In some embodiments, n is 3. In some embodiments, n 4. In some embodiments, n is 5. In some embodiments, n is 6. In some embodiments, n is 7. In some embodiments, n is 8. In some embodiments, n is 9. In some embodiments, n is 10.

In other different embodiments, the compound of structure (II) is selected from Table 3.

TABLE 3

Exemplary Compounds of Structure (II)

| # | Structure |
|---|---|
| II-1 | 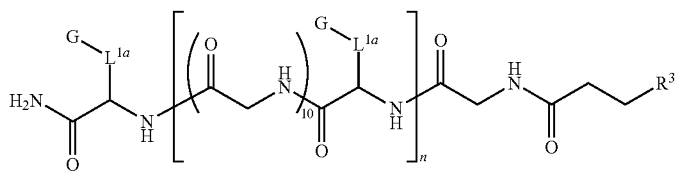 |
| II-2 | 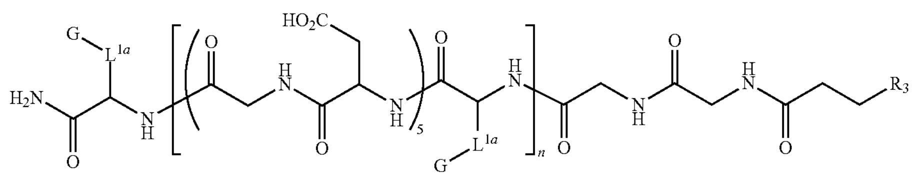 |
| II-3 | 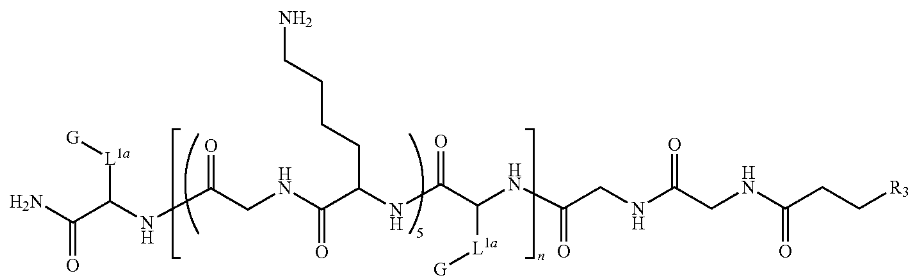 |
| II-4 | 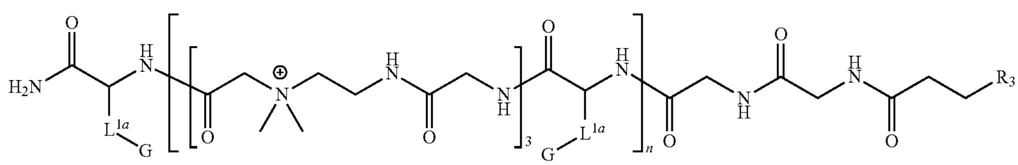 |
| II-5 | 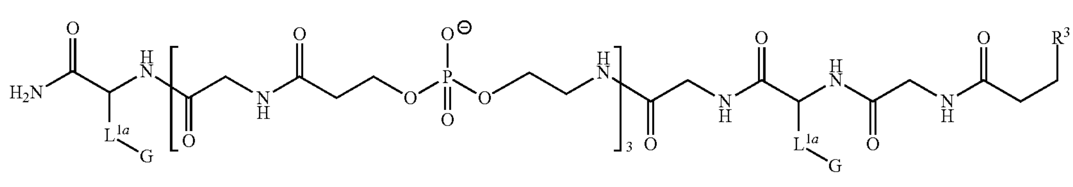 |
| II-6 | 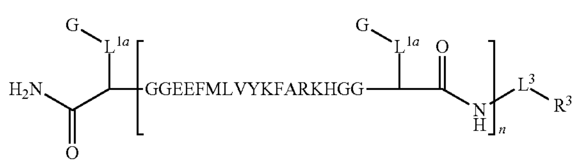 |
| II-7 | 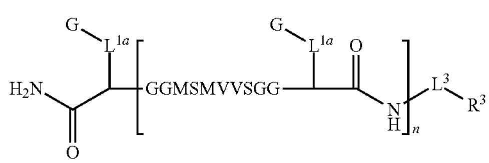 |

In various embodiments, G in the compounds of Table 3 is alkynyl, such as ethynyl. In other embodiments, G in the compounds of Table 3 is an azide.

The compounds of structure (II) can be used in various methods, for example in embodiments is provided a method for labeling an analyte molecule, the method comprising:

(a) admixing any of the described compounds of structure (II), wherein $R^2$ or $R^3$ is Q or a linker comprising a covalent bond to Q, with the analyte molecule;

(b) forming a conjugate of the compound and the analyte molecule; and (c) reacting the conjugate with a compound of formula M-$L^{1b}$-G', thereby forming at least one covalent bond by reaction of at least one G and at least one G', wherein:

M is a moiety comprising two or more carbon-carbon double bonds and at least one degree of conjugation;

$L^{1b}$ is an optional alkylene, heteroalkylene or heteroatomic linker; and

G' is a reactive group complementary to G.

A different embodiment is a method for labeling an analyte molecule, the method comprising:

(a) admixing any of the compounds of structure (II) disclosed herein, wherein $R^2$ or $R^3$ is Q or a linker comprising a covalent bond to Q, with a compound of formula M-$L^{1b}$-G', thereby forming at least one covalent bond by reaction of G and G'; and b) reacting the product of step (A) with the analyte molecule, thereby forming a conjugate of the product of step (A) and the analyte molecule, wherein:

M is a moiety comprising two or more carbon-carbon double bonds and at least one degree of conjugation;

$L^{1b}$ is an optional alkylene, heteroalkylene or heteroatomic linker; and

G' is a reactive group complementary to G.

Further, as noted above, the compounds of structure (II) are useful for preparation of compounds of structure (I). Accordingly, in one embodiment is provided a method for preparing a compound of structure (I), the method comprising admixing a compound of structure (II) with a compound of formula M-$L^{1b}$-G', thereby forming at least one covalent bond by reaction of G and G', wherein:

M is a moiety comprising two or more carbon-carbon double bonds and at least one degree of conjugation;

$L^{1b}$ is an optional alkylene, heteroalkylene or heteroatomic linker; and

G' is a reactive group complementary to G.

It is understood that any embodiment of the compounds of structure (I) or (II), as set forth above, and any specific choice set forth herein for a $R^1$, $R^2$, $R^3$, $L^1$, $L^{1a}$, $L^2$, $L^3$, $L^4$, $L^5$, m, G, m and n variable in the compounds of structure (I) or (II), as set forth above, may be independently combined with other embodiments and/or variables of the compounds of structure (I) or (II) to form embodiments of the inventions not specifically set forth above. In addition, in the event that a list of choices is listed for any particular $R^1$, $R^2$, $R^3$, $L^1$, $L^{1a}$, $L^2$, $L^3$, $L^4$, $L^5$, M, G, m and n variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3$^{rd}$ Ed., Wiley. As one of skill in the art would appreciate, the protecting group may also be a polymer resin such as a Wang resin, Rink resin or a 2-chlorotrityl-chloride resin.

Furthermore, all compounds of the invention (i.e., compounds of structure (I) and (II)) which exist in free base or acid form can be converted to their salts by treatment with the appropriate inorganic or organic base or acid by methods known to one skilled in the art. Salts of the compounds of the invention can be converted to their free base or acid form by standard techniques.

Exemplary methods of making compounds described herein are provided in the Examples. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5$^{th}$ edition (Wiley, December 2000)) or prepared as described in this invention.

The following examples are provided for purposes of illustration, not limitation.

EXAMPLES

General Methods $^1$H and NMR spectra are obtained on a JEOL 400 MHz spectrometer. $^1$H spectra are referenced against TMS. Reverse phase HPLC dye analysis is performed using a Waters Acquity UHPLC system with a 2.1 mm×50 mm Acquity BEH-C18 column held at 45° C. Mass spectral analysis is performed on a Waters/Micromass Quattro micro MS/MS system (in MS only mode) using MassLynx 4.1 acquisition software. Mobile phase used for LC/MS on dyes is 100 mM 1,1,1,3,3,3-hexafluoro-2-propanol (HFIP), 8.6 mM triethylamine (TEA), pH 8. Phosphoramidites and precursor molecules are analyzed using an Agilent Infinity 1260 UHPLC system with a diode array detector and High Performance Autosampler using an Aapptec© SPIRIT™ Peptide C18 column (4.6 mm×100 mm, 5 μm particle size).

Excitation and emission profiles experiments are recorded on a Cary Eclipse spectra photometer.

All reactions are carried out in oven dried glassware under a nitrogen atmosphere unless otherwise stated.

Example 1

GENERAL SYNTHESIS OF PEPTIDE BACKBONES VIA SOLID PHASE SYNTHESIS

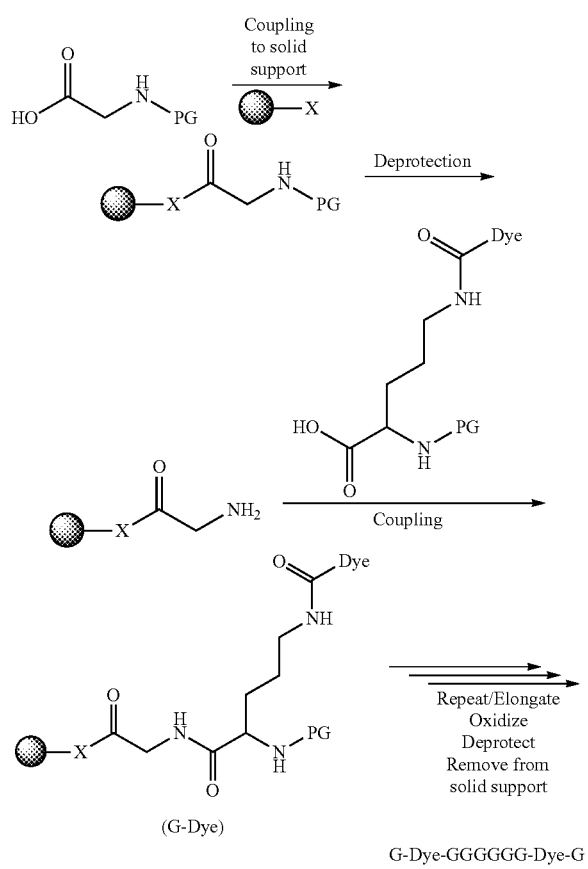

G-Dye-GGGGGG-Dye-G

The reaction scheme above illustrates an exemplary method for preparing an intermediate useful for preparation of compounds of structure (I), where PG is a suitable protecting group, X is a functional unit that a peptide chain can be built on, the shaded circle is a suitable solid support, and Dye is F', E', or Y'.

Small porous beads are initially treated with functional units, which bind to the surface of the porous beads. Peptide chains are built upon the functional units sites and remain covalently bonded to the bead until they are cleaved. When attached, a peptide chain is immobilized on the solid phase and retained during a filtration process, wherein liquid reagents and by-products of the synthesis are washed away.

The general cycle of solid phase synthesis is one of repeated cycles of deprotection-wash-coupling-wash. A free N-terminal amine of a peptide, attached to a solid support, is coupled to an N-protected amino acid group (e.g., with Fmoc or Boc). The newly introduced amino acid unit is deprotected to reveal a new N-terminal amine, which is further reacted with additional amino acids. The process is repeated and the peptide chain is elongated.

When the peptide chain has incorporated all desired amino acid and monomer units, it is cleaved from the bead. Cleaving reagents such as anhydrous hydrogen fluoride or trifluoroacetic acid can be used to cleave peptide chains from beads. The peptide chain is then collected, purified and characterized.

Example 2

General Characterization of Oligomer Dyes 1 mL of deionized water is added to the dried dye compound to re-constitute and establish a concentrated stock of ~0.3 to 1.0 mM (determined later). Aliquots of each dye construct are analyzed by HPLC-MS to determine identity and relative purity. Electrospray ionization is used to determine the molecular weights of the dye sequences and help to characterize impurities.

A sample is taken from a concentrated stock using a micropipettor and diluted appropriately in 0.1×PBS (10× to 100×) to be within linear range of the NanoDrop UV-vis spetrophotomer (Thermo Scientific). A blank measurement is performed on the NanoDrop using 0.1×PBS, and then the absorbance of the diluted dye sequence at an appropriate wavelength is recorded. Extinction coefficients ($\varepsilon$) are determined by the total number of fluors (M moieties) in the dye construct, using 75,000 $M^{-1}$ $cm^{-1}$ for each fluorescein (F'; read at 494 nm); 34,500 for each pyrene (Y'; read at 343 nm); and 40,000 for each perylene (E'; read at 440 nm) present in the sequence. Spacers are presumed to have no effect on $\varepsilon$.

Molar concentration of dye is determined according to the formula $\{A_{494}/(L^*\varepsilon_{Dye})\}$*Dilution Factor. With concentration determined, the dye stock is diluted in the $NaPO_4$ (0.1 M at pH 7.5) and $NaCO_3$ (0.1 M at pH 9.0) buffers to make solutions of 2 μM (or 5 μM, whatever works with the linear range of the instrument) at a final volume of ~3.5 mL. These solutions are scanned by UV/Vis, and then used to make a second dilution in the appropriate buffer for reading on the fluorimeter, in the range of 10-50 nM. The necessary concentration will vary depending upon the identity of the M moiety.

Example 3

General Flow Cytometry Method and Applications

The general flow cytometry workflow includes the following steps:
1. Culture and visually observe cells for signs of metabolic stress and/or use fresh, induced, or simulated cells.
2. Dilute dye compounds to working volumes.
3. Harvest and prepare cells without killing or inducing apoptosis.
4. Centrifuge and wash cells with appropriate buffer.
5. Perform cell counts using hemocytometer and trypan blue exclusion.
6. Centrifuge and wash cells
7. Adjust cell density to test size
8. Apply dye (pre-dilution) or other co-stains of interest.
9. Incubate the cell/stain/dye mixture.
10. Centrifuge and wash cells with appropriate buffer.
11. Re-suspend cells in acquisition buffer.
12. Acquire cell data by flow cytometry.

The general workflow described above can be modified accord to specific applications. Some modifications for specific applications are described below.

Live/Dead Discrimination

Cells are tested for viability by positively staining necrotic cells to compare damaged cells to intact cells. Assays are used to target non-intact (fixed and non-fixed) cells with positively charged moieties, cell debris, apoptotic bodies, depolarized cell membrane, and permeabilized membranes. Cells are then stained with dye using routine cell preparations (fresh or fixed) and analyzed using flow cytometry.

Cell Health

A comparison is made between dead cells (i.e., necrotic cells), early apoptotic, late apoptotic, and live cells. Dead cells are positively stained, Apoptotic bodies are intermediately stained, and live cells are left negative. This strategy results in very bright necrotic cells and works also to assess cell permeability. Assays are used to target non-intact (fixed and non-fixed) cells with positively charged moieties, cell debris, apoptotic bodies, depolarized cell membrane, and permeabilized membranes. Dye staining is performed on in vitro cultures, primary cells, and samples treated with xenobiotics and analyzed using flow cytometry.

Cell Cycle

Cell ploidy and mitosis is the cell cycle is tracked by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with other dyes) is performed on in vitro cultures, primary cells, and samples treated with xenobiotics and analyzed using flow cytometry.

Proliferation

Cell proliferation is monitored by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with monitoring markers for cell proliferation, e.g. Ki67, BRDU) is performed on in vitro cultures, primary cells, and samples treated with xenobiotics and analyzed using flow cytometry.

Example 4

Cell Culture of Jurkat Cells

Jurkat cells (Clone E6-1; ATCC® TIB-152™) are human lymphocyte cells found in peripheral blood tissue and used to model acute T cell Leukemia. Cells are cultured in RPMI-1640 Medium, fetal bovine serum 10%, 0.1 M HEPES, PenStrep and L-glutamine.

Cultures are maintained by addition of fresh medium or replacement of medium between $1\times10^5$ viable cells/mL and $5\times10^6$ cells/mL. Alternatively, cultures are established by centrifugation with subsequent resuspension at $1\times10^5$ viable cells/mL. Fresh medium is added every 2 to 3 days depending on cell density.

Example 5

Cell Culture of Ramos Cells

Ramos (RA 1; ATCC CRL-1596) are human B lymphocytes and are used to model Burkitt's Lymphoma (American). Cells are cultured in RPMI-1640 Medium with heat-inactivated fetal bovine serum 10%, 0.1 HEPES, PenStrep and L-glutamine.

Cultures are maintained by addition of fresh medium or replacement of medium between $1\times10^5$ viable cells/mL and $5\times10^6$ cells/mL. Alternatively, cultures are established by centrifugation with subsequent resuspension at $1\times10^5$ viable cells/mL. Fresh medium is added every 2 to 3 days depending on cell density.

Example 6

General Procedure for Inducing Cell Death and Recovering Dead Cells

Cultured cells are induced into necrosis and apoptosis in vitro to form dead cells, cell debris, and apoptotic bodies. Cells are induced by introducing heat stress and/or metabolic stress. Heat stress is performed by subjecting cultures to 57-60° C. for 3-5 minutes and then transferring cell cultures to ice for 10 minutes. Metabolic stress is performed by post log phase growth crowding, toxin, or xenobiotic treatment (e.g. 10 nM maptothecin). Fresh cells are maintained by subjecting cultures to no treatment.

Cell preparations are re-suspended in staining buffer, and then mixed in ratios to target a viable population of intact cells between 60-80% (i.e., 20-40% non-intact cellular debris-like events as measured by morphology using flow cytometry parameters FSC v. SSC). Cell viability is verified microscopically by Live/Dead trypan blue exclusion or by 7-aminoactinomycin D (7-AAD) by flow cytometry. In some experiments, mixtures of induced/non-induced cells are unnecessary. Instead, a post-log phase growth culture undergoing metabolic stress containing 30-40% necrotic and apoptotic cells is used.

Example 7

Inducing Cell Death and Recovery of Dead Cells for Jurkat and Ramos Cells

Mid-log phase Jurkat and Ramos or primary PBMC cells are induced into necrosis in vitro in order to form dead cells and cell debris. Cells are induced by heat stress by subjecting cultured cells first to 58° C. for 3-5 minutes, then transferring them to ice for 10-15 minutes. Fresh cells are maintained by subjecting cultures to no treatment.

Cells are resuspended in 1×DBS with $Ca^{++}/Mg^{++}$ at a cell density of $10\times10^6$ cells/mL. Fresh cells (~8% necrotic) and stressed cells (~20% necrotic) are then mixed in the following ratios to produce a measurable gradient of viable to necrotic cells:

1. 100% live:0% dead
2. 50% live:50% dead
3. 25% live:75% dead
4. 12.75% no induction:85.25% induced
5. 6% no induction:94% induced The expected viability ranges from 8-30%. Starting and ending viabilities are verified by 7-Aminoactinomycin D (7-AAD) by flow cytometry or trypan blue exclusion.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (I):

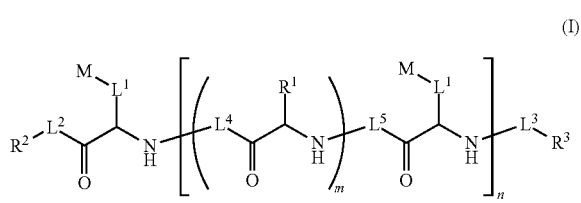

or a stereoisomer, salt or tautomer thereof, wherein:
M is, at each occurrence, independently a fluorescent or colored moiety comprising two or more carbon-carbon double bonds and at least one degree of conjugation;
$L^1$ is at each occurrence, independently either: i) an optional alkylene, alkenylene, alkynylene, heteroalkylene, heteroalkenylene or heteroalkynylene linker; or ii) a linker comprising a functional group capable of formation by reaction of two complementary reactive groups;
$L^2$, $L^3$, $L^4$ and $L^5$ are, at each occurrence, independently optional alkylene, alkenylene, alkynylene, heteroalkylene, heteroalkenylene or heteroalkynylene linkers;
$R^1$ is, at each occurrence, independently a natural or unnatural amino acid side chain;
$R^2$ and $R^3$ are each independently H, —OH, —SH, —NH$_2$, —CO$_2$H, alkyl, alkylether, alkoxy, heteroalkyl, alkylaminyl, alkylcarbonyl, alkyloxycarbonyl, Q, a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue or a linker comprising a covalent bond to a further compound of structure (I), wherein the alkyl, alkylether, alkylaminyl, alkylcarbonyl and alkyloxycarbonyl are optionally substituted with hydroxyl, amino, sulfhydryl, phosphate, thiophosphate, phosphoalkyl, thiophosphoalkyl, phosphoalkylether or thiophosphoalkylether, or combinations thereof; Q is, at each occurrence, independently a moiety comprising a reactive group capable of forming a covalent bond with an analyte molecule, a solid support or a complementary reactive group Q';
m is, at each occurrence, independently an integer of zero or greater; and
n is an integer of one or greater.

2. The compound of claim 1, wherein $R^1$ is, at each occurrence, independently H, alkyl, —CH$_2$CO$_2^-$, —CH$_2$CH$_2$CO$_2^-$, —CH$_2$CH$_2$CH$_2$NH$_3^+$, —CH$_2$CH$_2$CH$_2$NHC(=NH$_2^+$)NH$_2$ or imidazolyl.

3. The compound of claim 1, wherein $R^1$, $L^4$ and m are selected such that

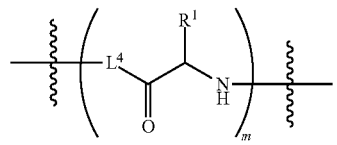

has an amino acid sequence of (G)$_{10}$, (GDGDGDGDGD) or (GKGKGKGKGK).

4. The compound of claim 1, wherein $R^1$, $L^4$ and m are selected such that

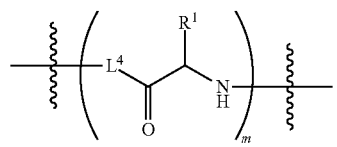

has an amino acid sequence capable of forming an α-helix or β-sheet secondary structure.

5. The compound of claim 4, wherein the amino acid sequence is (GGEEFMLVYKFARKHGG) or (GGMSMVVSGG).

6. The compound of claim 1, wherein $L^4$ and $L^5$ are absent at each occurrence.

7. The compound of claim 1, wherein at least one occurrence of $L^4$ or $L^5$, or both, has the following structure:

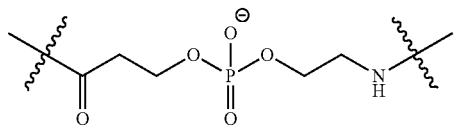

8. The compound of claim 1, wherein at least one occurrence of $L^4$ or $L^5$, or both, has the following structure:

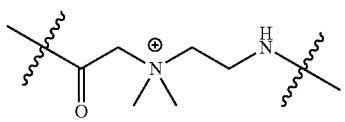

9. The compound of claim 1, wherein L' is at each occurrence an alkylene or heteroalkylene linker.

10. The compound of claim 1, wherein $L^1$ is at each occurrence a linker comprising a functional group capable of formation by reaction of two complementary reactive groups and for at least one occurrence of $L^1$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group with a complementary reactive group.

11. The compound of claim 10, wherein for at least one occurrence of $L^1$, $L^1$-M has the following structure:

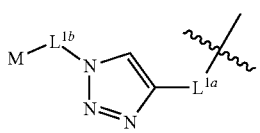

wherein L$^{1a}$ and L$^{1b}$ are each independently optional linkers.

12. The compound of claim 10, wherein for at least one occurrence of L$^1$, L$^1$-M has the following structure:

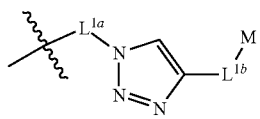

wherein L$^{1a}$ and L$^{1b}$ are each independently optional linkers.

13. The compound of claim 1, wherein R$^2$ is —NH$_2$.

14. The compound of claim 1, wherein Q has one of the following structures:

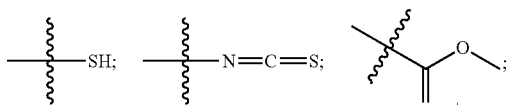

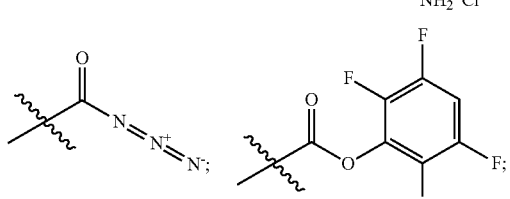

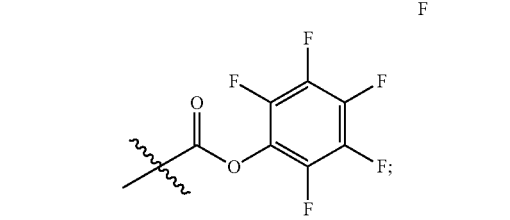

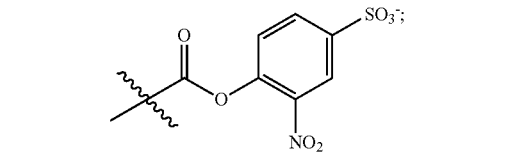

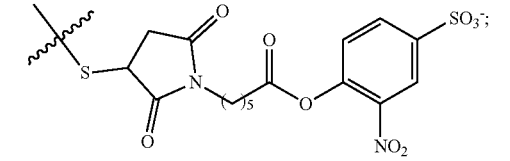

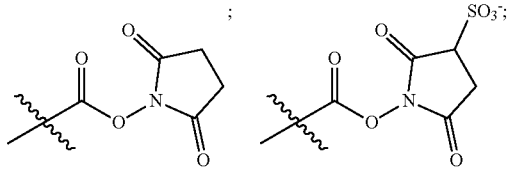

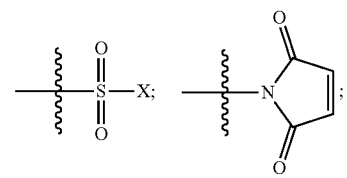

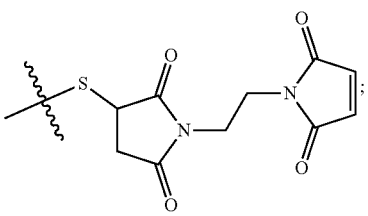

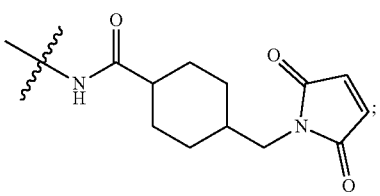

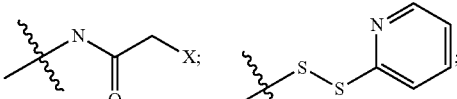

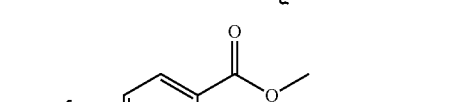

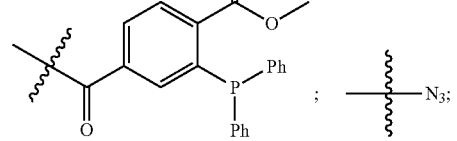

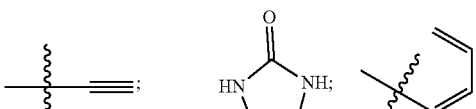

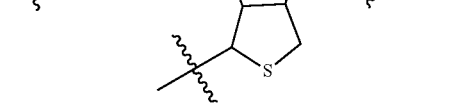

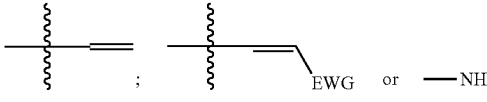

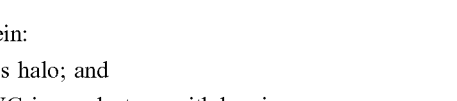

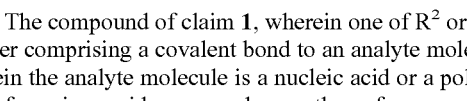

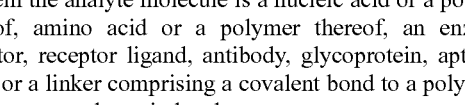

wherein:

X is halo; and

EWG is an electron withdrawing group.

15. The compound of claim 1, wherein one of R$^2$ or R$^3$ is a linker comprising a covalent bond to an analyte molecule, wherein the analyte molecule is a nucleic acid or a polymer thereof, amino acid or a polymer thereof, an enzyme, receptor, receptor ligand, antibody, glycoprotein, aptamer, prion or a linker comprising a covalent bond to a polymeric bead or non-polymeric bead.

16. The compound of claim 1, wherein M is, at each occurrence, independently a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety.

17. The compound of claim 1, wherein M, at each occurrence, independently has one of the following structures:

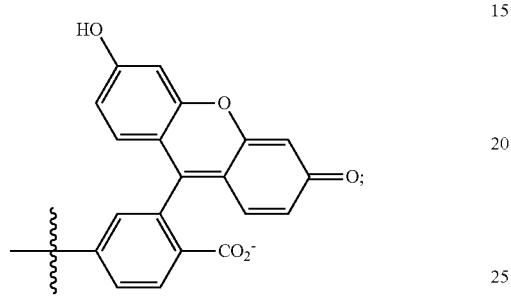

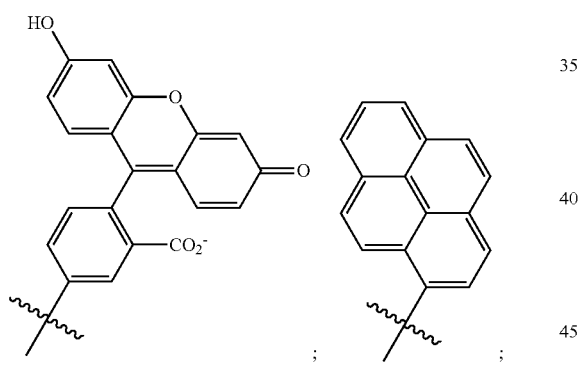

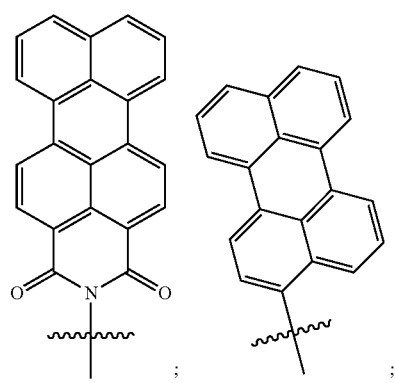

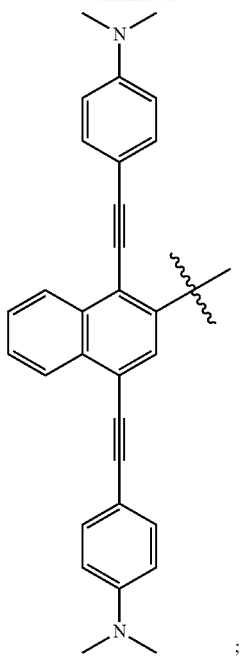

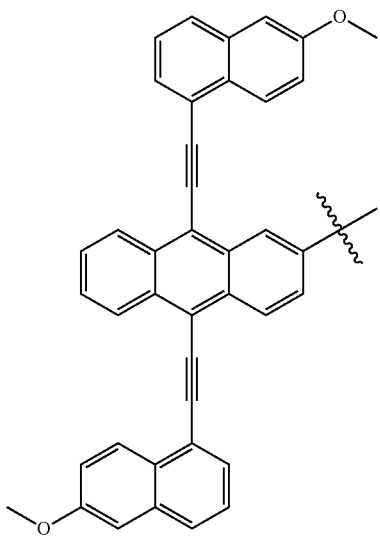

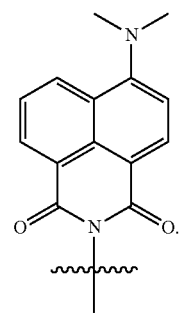

18. The compound of claim 1, wherein the compound has one of the following structures:

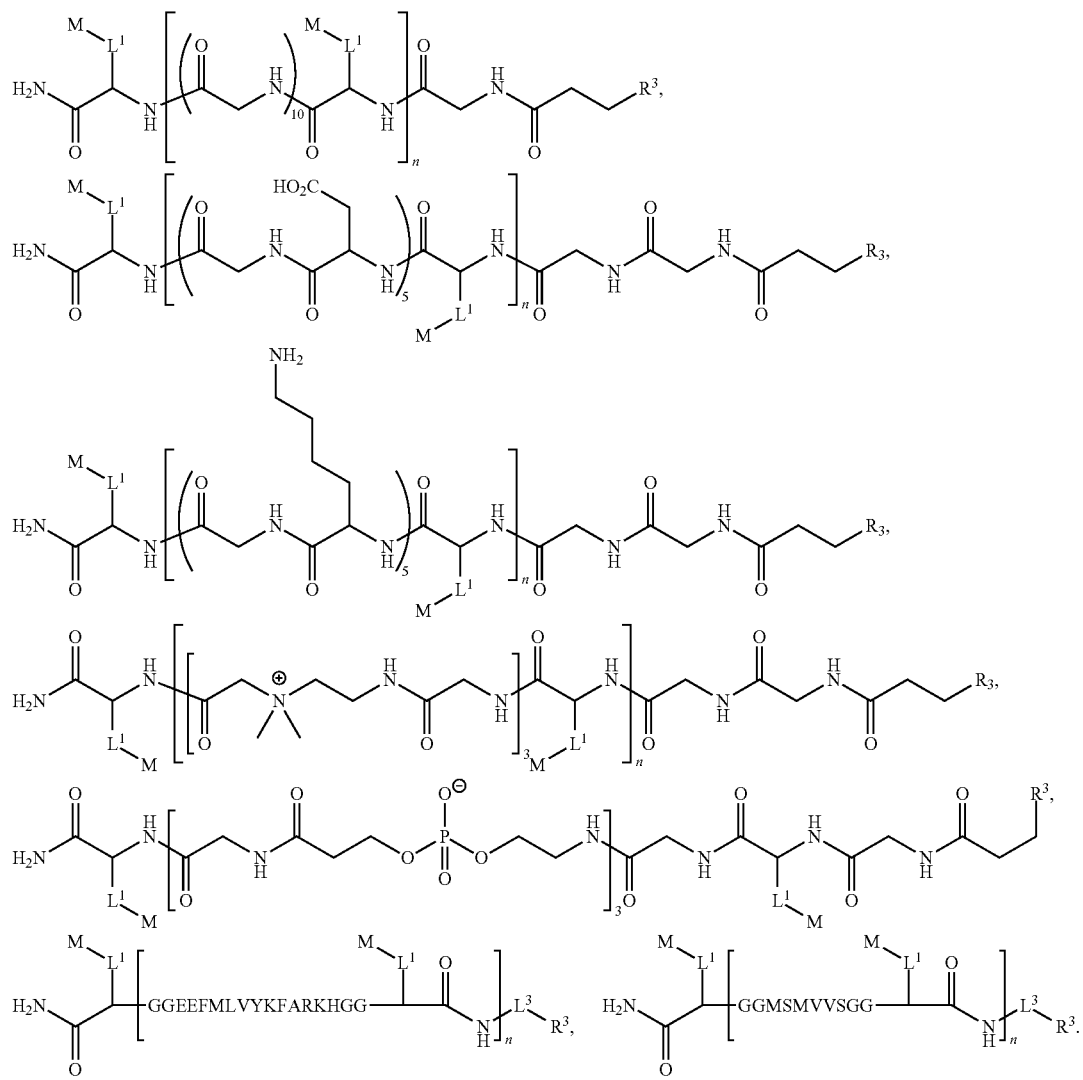

19. A method of staining a sample, comprising adding to said sample the compound of claim 1 in an amount sufficient to produce an optical response when said sample is illuminated at an appropriate wavelength.

20. A compound having the following structure (II):

(II)

or a stereoisomer, salt or tautomer thereof, wherein:
G is, at each occurrence, independently a moiety comprising a reactive group capable of forming a covalent bond with a complementary reactive group;
$L^{1a}$, $L^2$, $L^3$, $L^4$ and $L^5$ are, at each occurrence, independently an optional alkylene, alkenylene, alkynylene, heteroalkylene, heteroalkenylene or heteroalkynylene linker;
$R^1$ is, at each occurrence, independently a natural or unnatural amino acid side chain;
$R^2$ and $R^3$ are each independently H, —OH, —SH, —NH$_2$, —CO$_2$H, alkyl, alkylether, alkoxy, heteroalkyl, alkylaminyl, alkylcarbonyl, alkyloxycarbonyl, Q, a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue or a linker comprising a covalent bond to a further compound of structure (I), wherein the alkyl, alkylether, alkylaminyl, alkylcarbonyl and alkyloxycarbonyl are optionally substituted with hydroxyl, amino, sulfhydryl, phosphate, thiophosphate, phosphoalkyl, thiophosphoalkyl, phosphoalkylether or thiophosphoalkylether, or combinations thereof;
Q is, at each occurrence, independently a moiety comprising a reactive group capable of forming a covalent bond with an analyte molecule, a solid support or a complementary reactive group Q';
m is, at each occurrence, independently an integer of zero or greater; and
n is an integer of one or greater.

* * * * *